United States Patent
Nishiyama et al.

(10) Patent No.: US 7,341,694 B2
(45) Date of Patent: Mar. 11, 2008

(54) AMMONIA SENSOR

(75) Inventors: Hiroyuki Nishiyama, Aichi (JP); Shiro Kakimoto, Aichi (JP); Ryuji Inoue, Gifu (JP); Hitoshi Yokoi, Aichi (JP); Noboru Ishida, Gifu (JP); Takafumi Oshima, Aichi (JP); Satoshi Sugaya, Aichi (JP); Koichi Imaeda, Aichi (JP); Tadashi Hattori, Aichi (JP); Atsushi Satsuma, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 828 days.

(21) Appl. No.: 10/669,660

(22) Filed: Sep. 25, 2003

(65) Prior Publication Data

US 2004/0132202 A1 Jul. 8, 2004

(30) Foreign Application Priority Data

| Sep. 25, 2002 | (JP) | ............................. 2002-279680 |
| Feb. 27, 2003 | (JP) | ............................. 2003-051346 |
| Jul. 16, 2003 | (JP) | ............................. 2003-275327 |

(51) Int. Cl.
G01N 27/04 (2006.01)
G01N 33/00 (2006.01)

(52) U.S. Cl. ..................... 422/90; 73/31.06; 422/83; 422/88; 422/98; 436/111; 436/113; 436/151; 436/181

(58) Field of Classification Search .... 73/31.05–31.06; 422/83, 88, 90, 98; 436/108, 111, 113, 149, 436/151, 163, 181
See application file for complete search history.

(56) References Cited

U.S. PATENT DOCUMENTS

| 5,143,696 A | 9/1992 | Haas et al. |
| 5,546,004 A * | 8/1996 | Schmelz ..................... 324/446 |
| 6,069,013 A | 5/2000 | Plog et al. |
| 2002/0146352 A1* | 10/2002 | Wang et al. .................. 422/96 |
| 2003/0066519 A1* | 4/2003 | Wachsman et al. ......... 123/703 |

FOREIGN PATENT DOCUMENTS

| EP | 1 008 847 A2 | | 6/2000 |
| GB | 2166247 | * | 4/1986 |
| JP | 4-29049 | * | 1/1992 |
| JP | 5-45319 | | 2/1993 |

(Continued)

OTHER PUBLICATIONS

Mitsuhashi, H. et al, Chemistry Express 1992, 7, 409-412.*
Takao, Y. et al, Journal of the Electrochemical Society 1994, 141, 1028-1034.*

(Continued)

*Primary Examiner*—Arlen Soderquist
(74) *Attorney, Agent, or Firm*—Sughrue Mion, PLLC

(57) ABSTRACT

In an ammonia sensor (1), lead portions (7) and (9) are provided on an insulating substrate (5); a pair of comb-shaped electrodes (11) and (13) are connected to the lead portions (7) and (9), respectively; a sensitive layer (15) is provided on the comb-shaped electrodes (11) and (13); and a protective layer (17) is provided on the sensitive layer (15). Particularly, the sensitive layer (15) is formed of a gas-sensitive raw material predominantly containing $ZrO_2$ and containing at least W in an amount of 2 to 40 wt. % as reduced to $WO_3$.

27 Claims, 17 Drawing Sheets

FOREIGN PATENT DOCUMENTS

| JP | 05-087760 A | | 6/1993 |
|---|---|---|---|
| JP | 10-019821 A | | 1/1998 |
| JP | 10-221286 A | | 8/1998 |
| JP | 11-10000 | | 1/1999 |
| JP | 2000-55854 | * | 2/2000 |

OTHER PUBLICATIONS

Miura, N. et al, Sensors and Actuators, B 1996, 34, 367-372.*

Yun, D. H. et al, Transducers 97, International Conference on Solid-State Sensors and Actuators, Chicago, Jun. 16-19, 1997, vol. 2, 959-962, Publisher: Institute of Electrical and Electronics Engineers, New York, N. Y.*

Shimizu, Y. et al, Journal of Molecular Catalysis A: Chemical 2000, 155, 183-191.*

U. Simon et al.; "The effect of $NH_3$ on the ionic conductivity of dehydrated zeolites Na beta and H beta"; Microporous and Mesoporous Materials 21 (1998) pp. 111-116.

Ralf Moos et al.; "Selective Ammonia Exhaust Gas Sensor for Automotive Applications"; Transducers '01 Eurosensors XV, The 11th International Conference on Solid-State Sensors and Actuators, Digest of Technical Papers, vol. 1/2, Jun. 10-14, 2001.

A.R. Raju et al.; "$MoO_3/TiO_2$ and $Bi_2MoO_6$ as ammonia sensors"; Sensors and Actuators B Chemical; vol. B21, No. 1, Jul. 1994, pp. 23-26.

* cited by examiner

[FIG. 1]
W-CONTAINING SUPER-STRONG ACIDIC METAL OXIDE
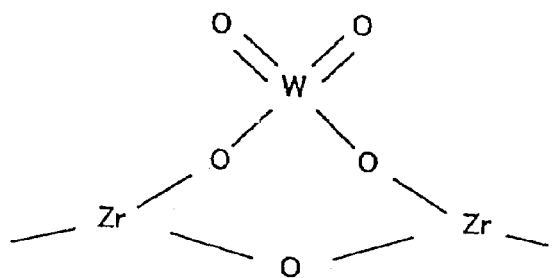
SULFATED SUPER-STRONG ACIDIC METAL OXIDE
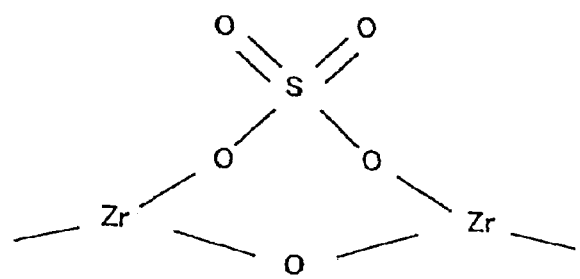
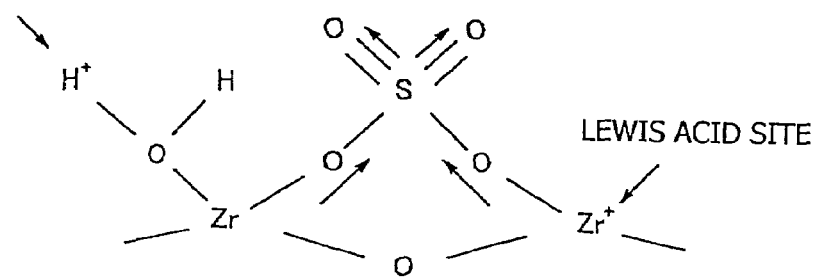

[FIG. 2]
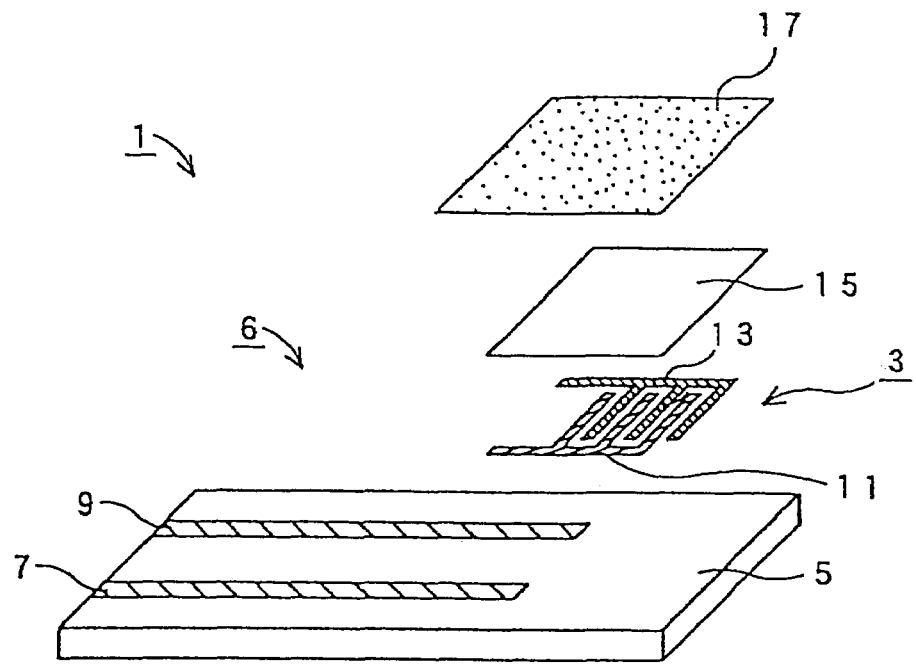
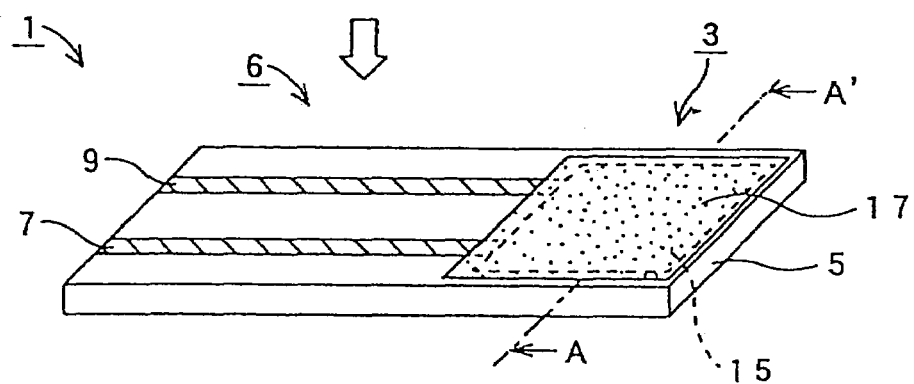
[FIG. 3]
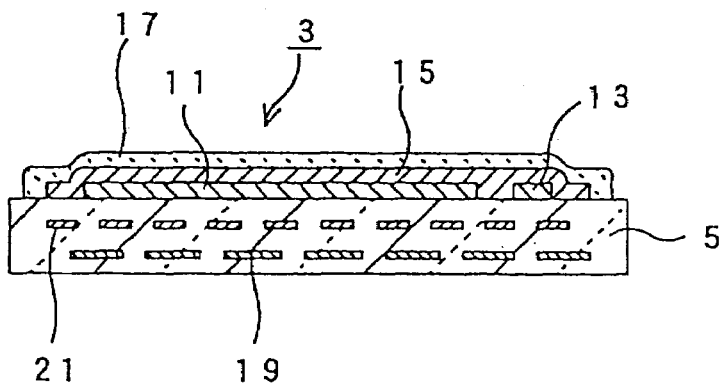

[FIG. 4]
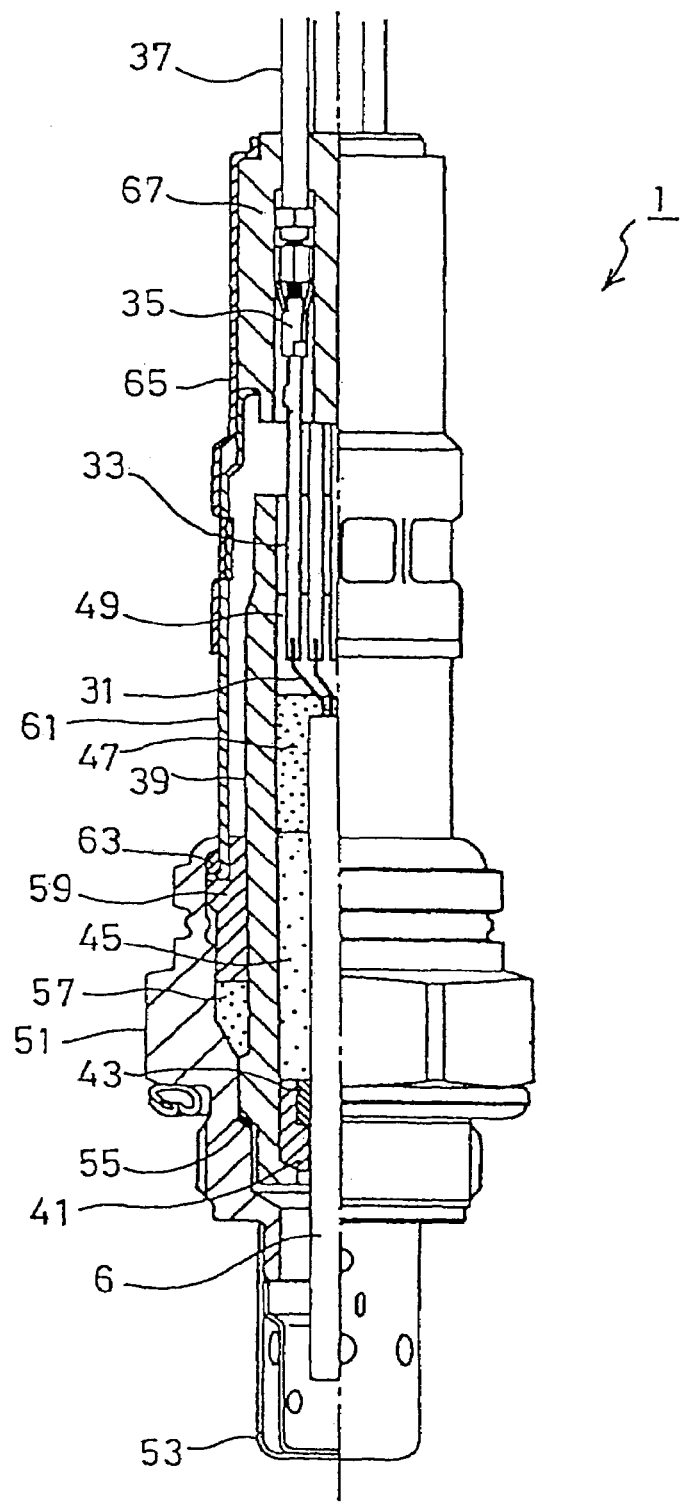

[FIG. 5]
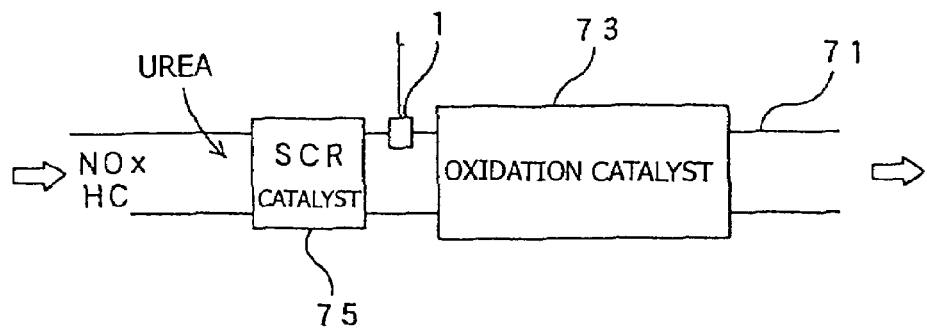
[FIG. 6]
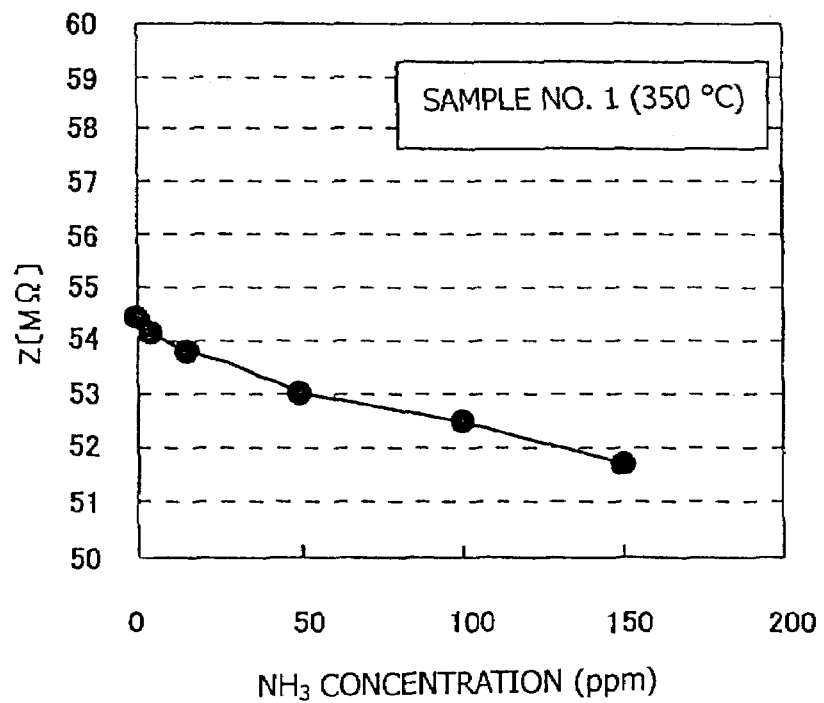

[FIG. 7]
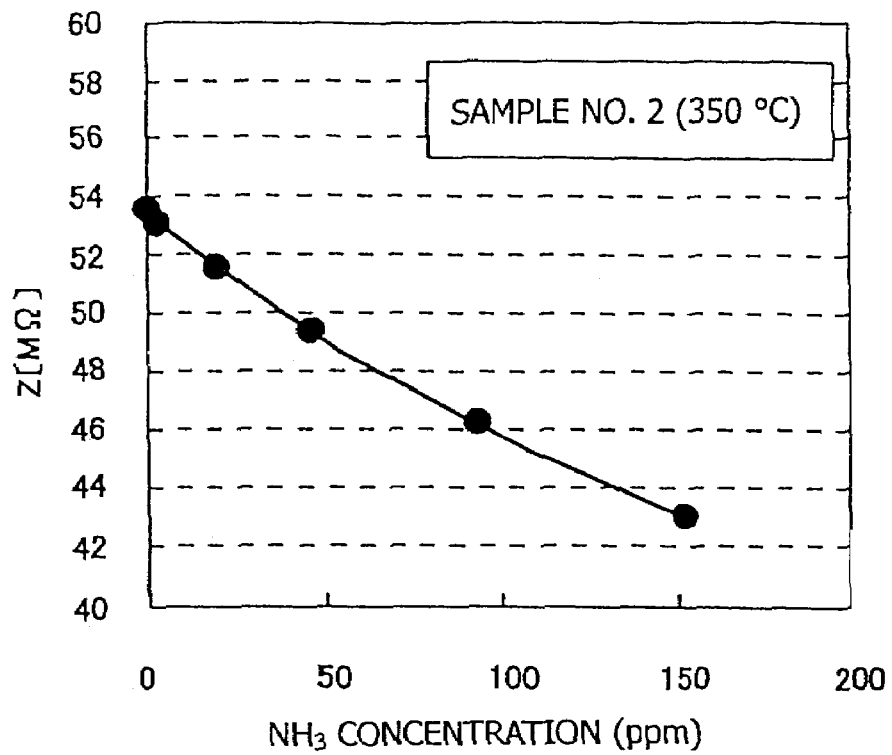
[FIG. 8]
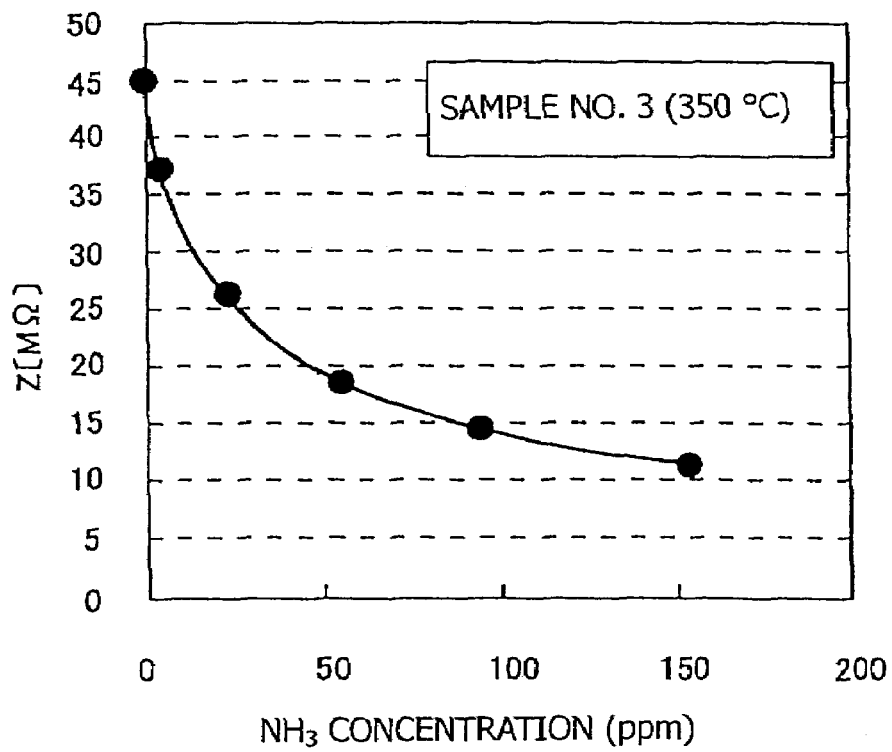

[FIG. 9]
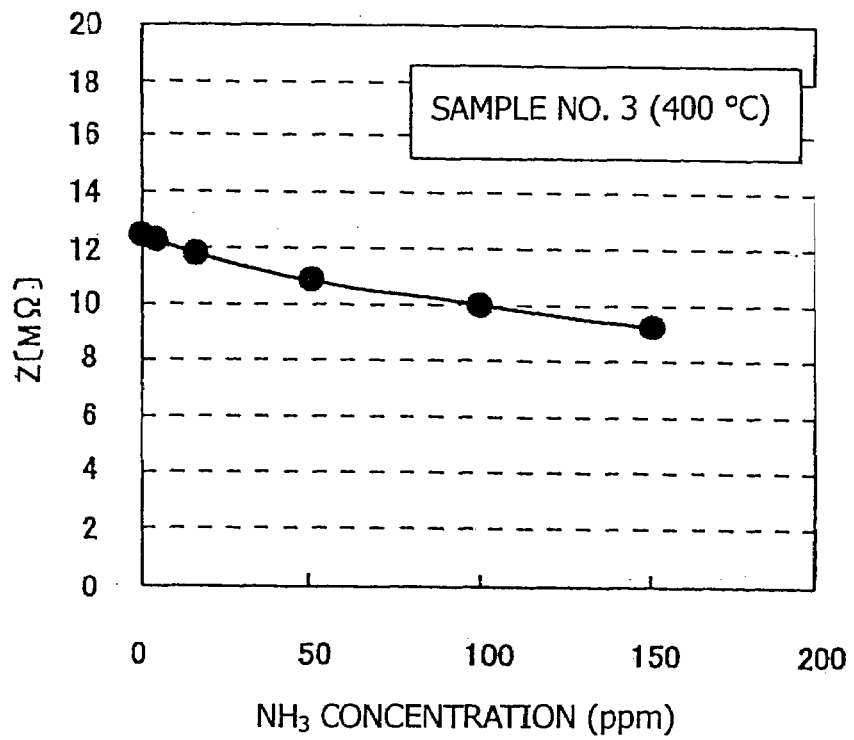
[FIG. 10]
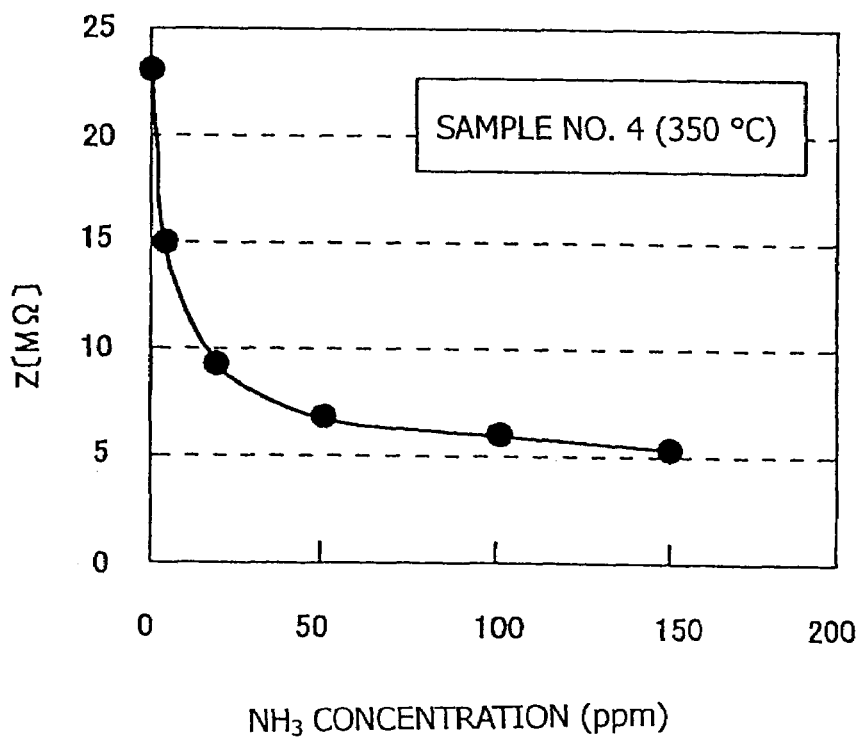

[FIG. 11]
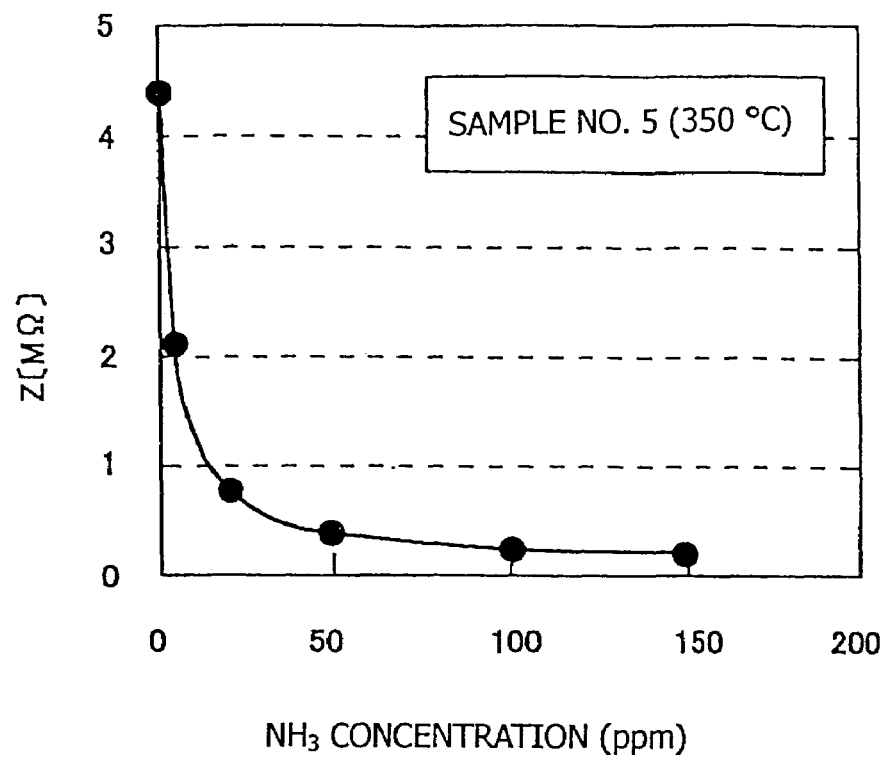
[FIG. 12]
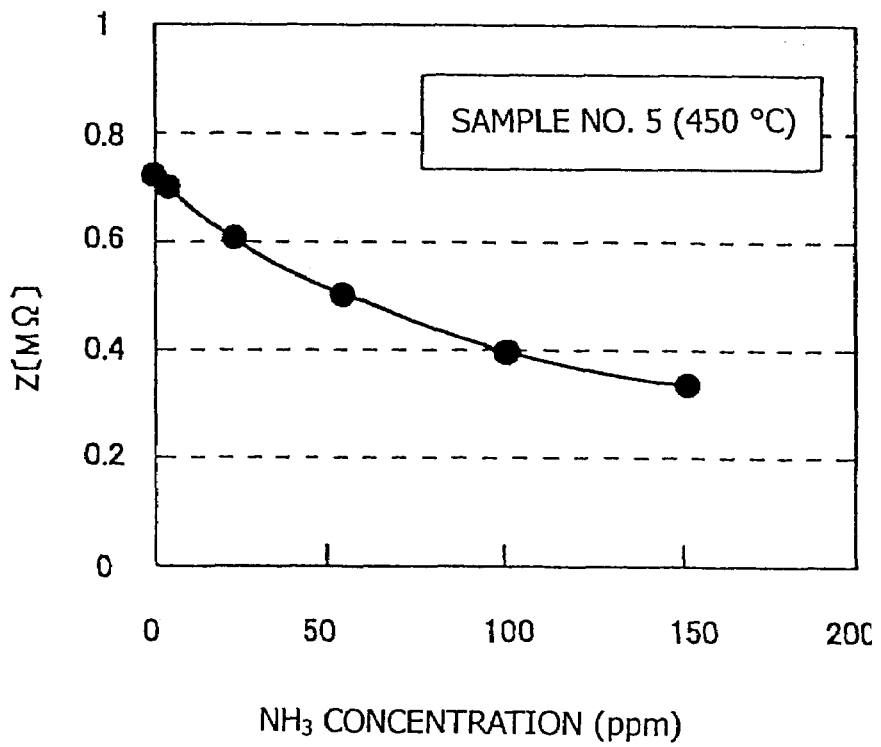

[FIG. 13]
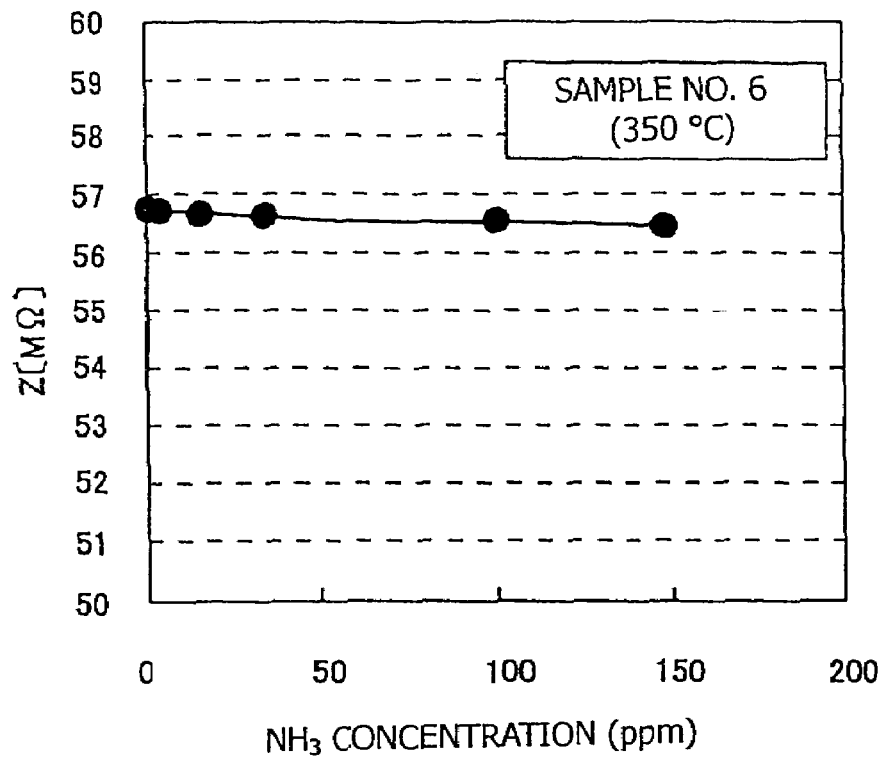
[FIG. 14]
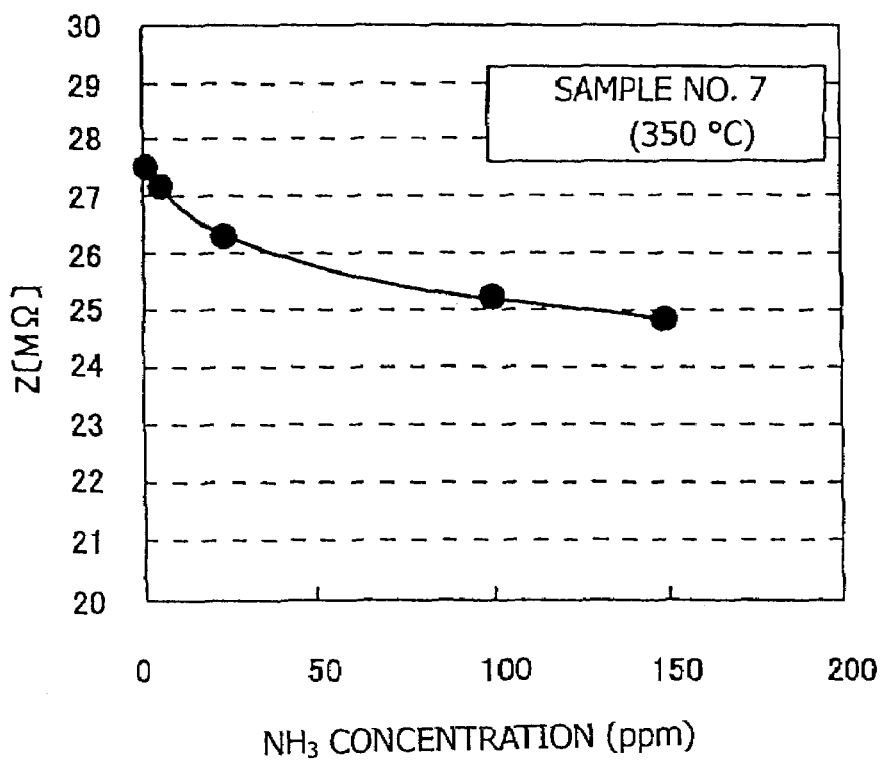

[FIG. 15]
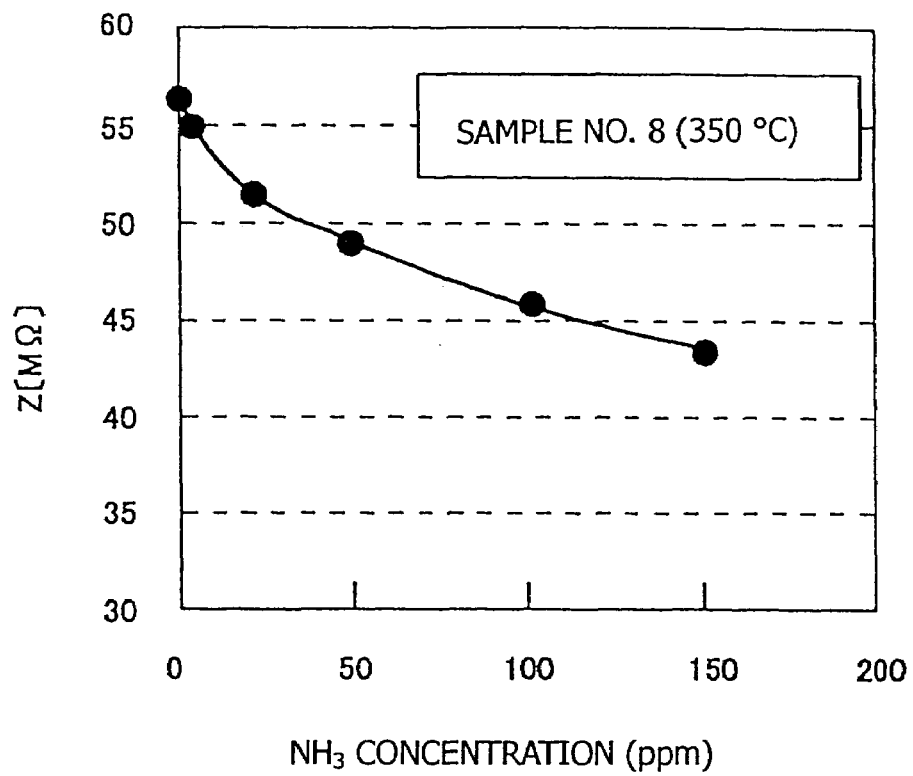
[FIG. 16]
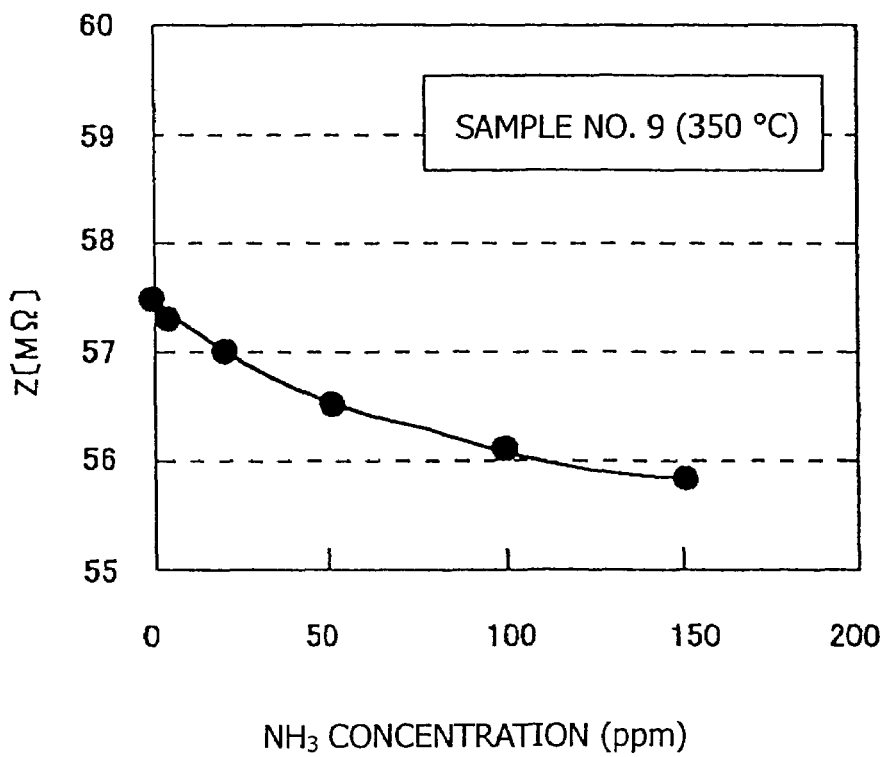

[FIG. 17]
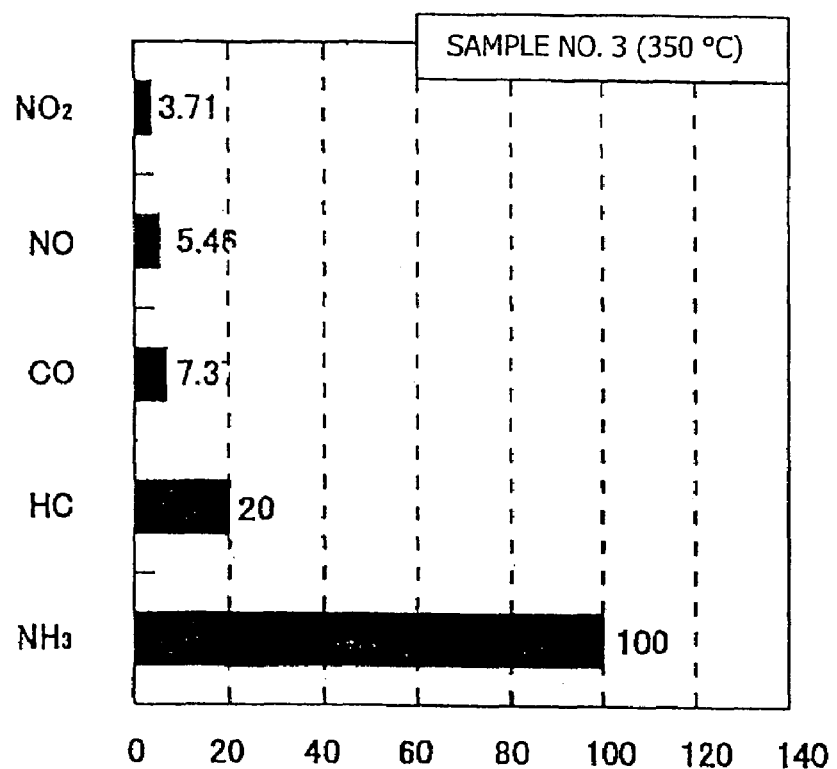
[FIG. 18]
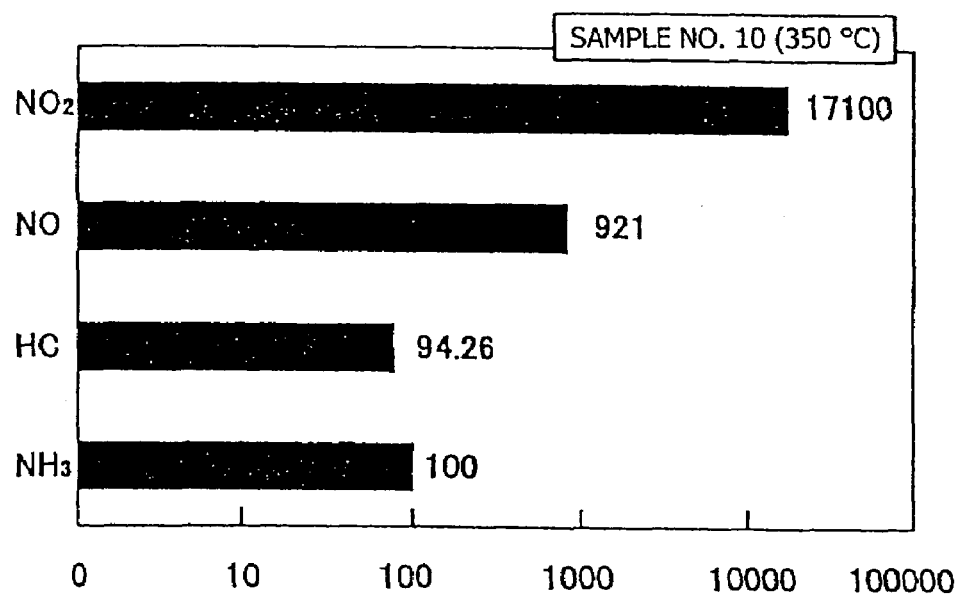

[FIG. 19]
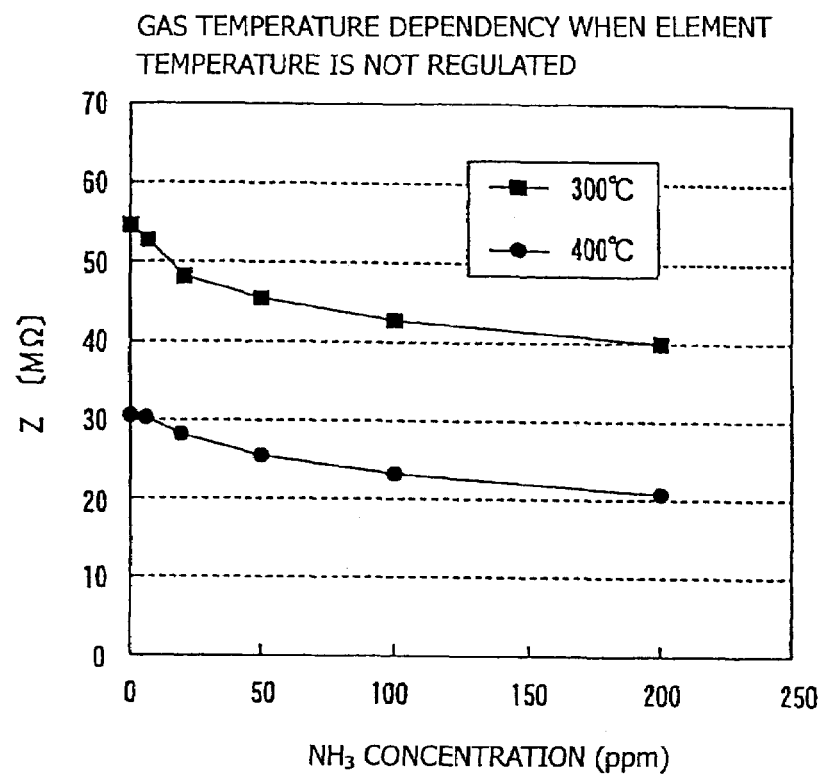
[FIG. 20]
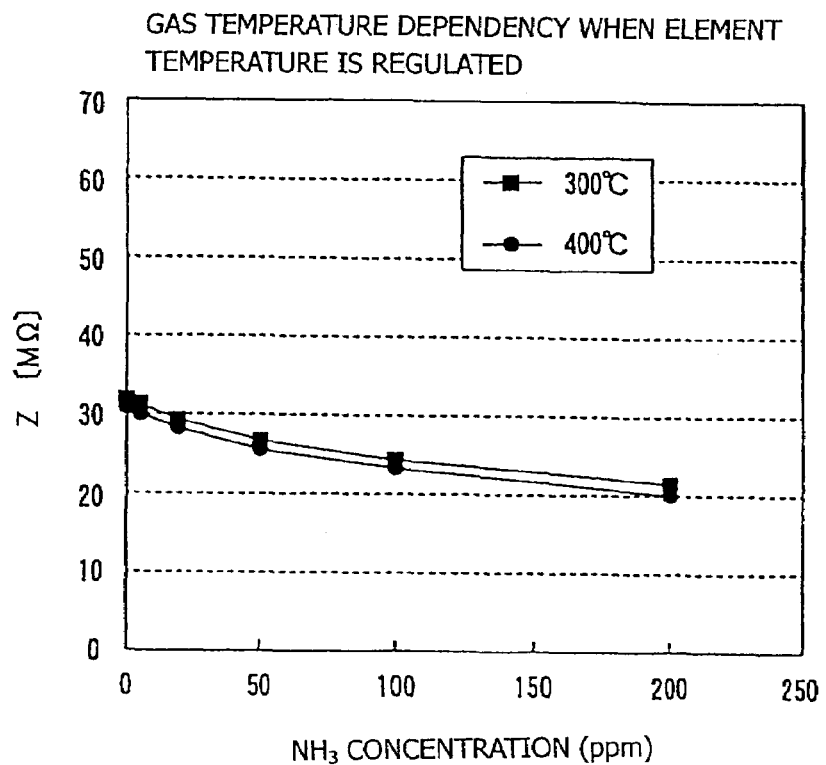

[FIG. 21]
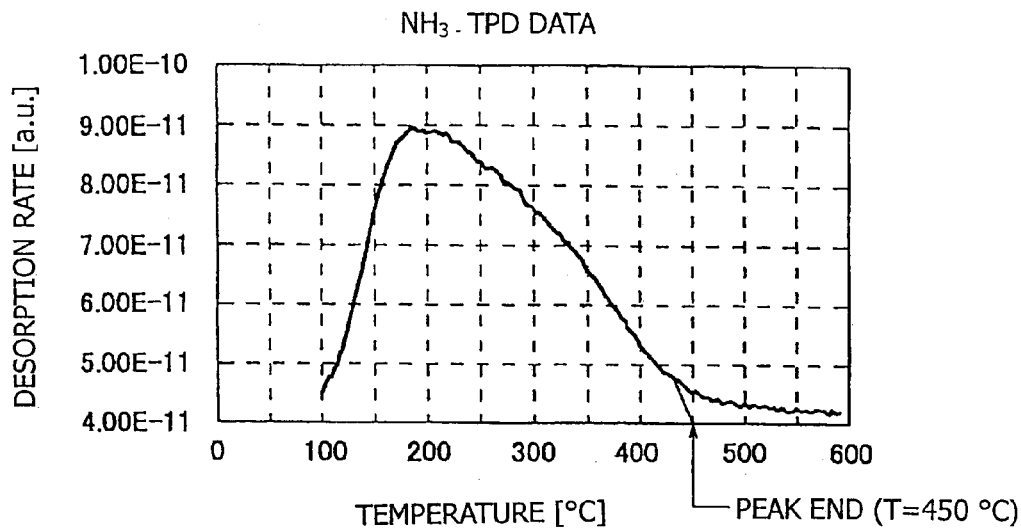
[FIG. 22]
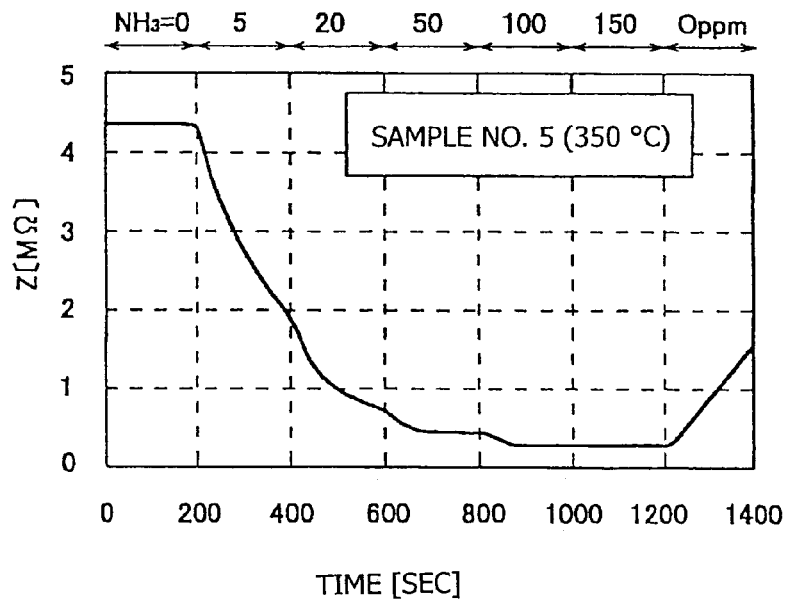

[FIG. 23]
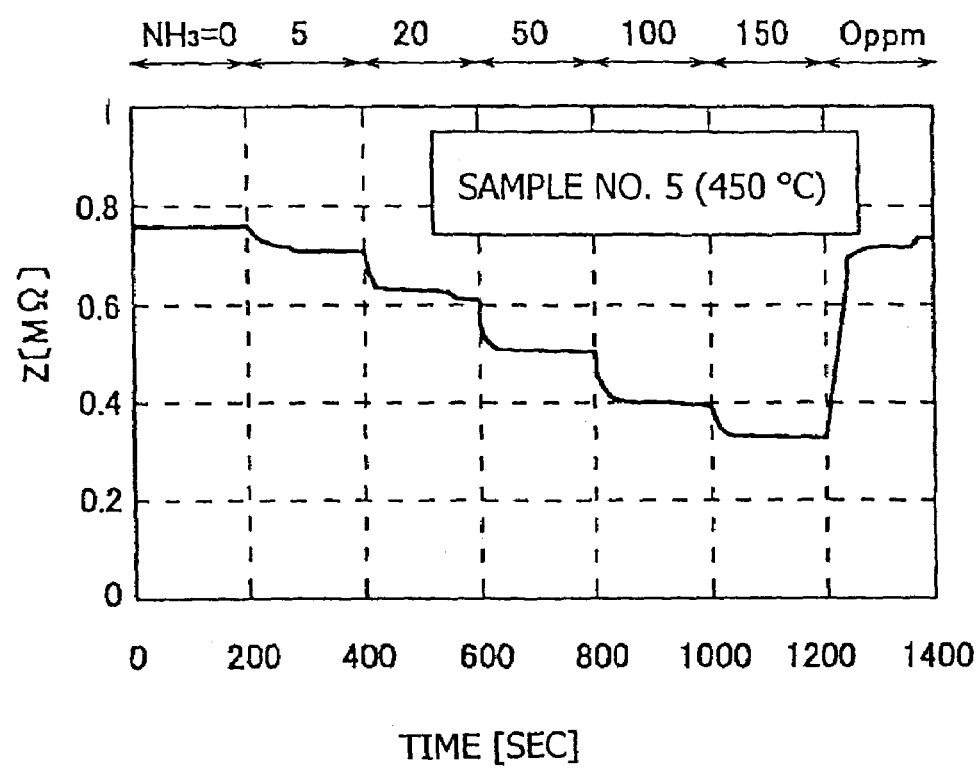

[FIG. 24]
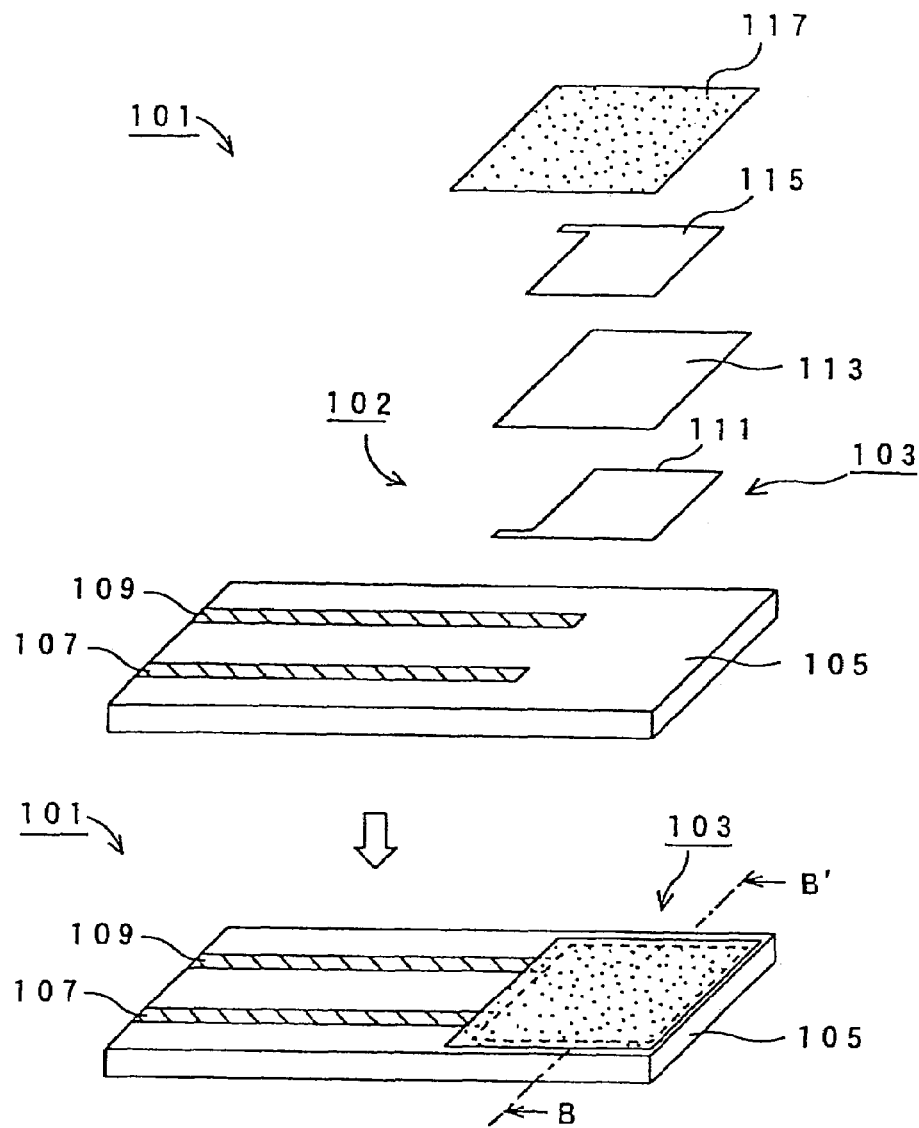
[FIG. 25]
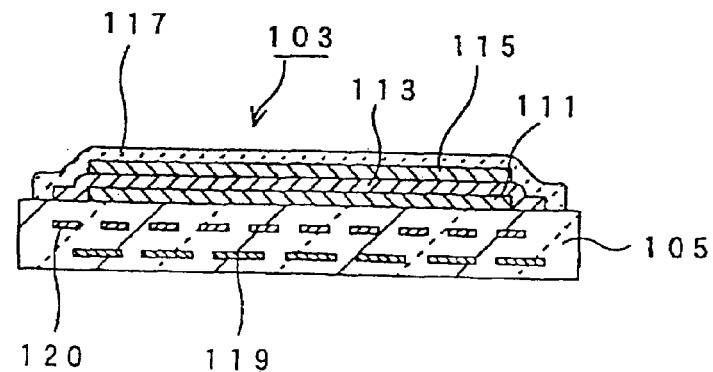

[FIG. 26]
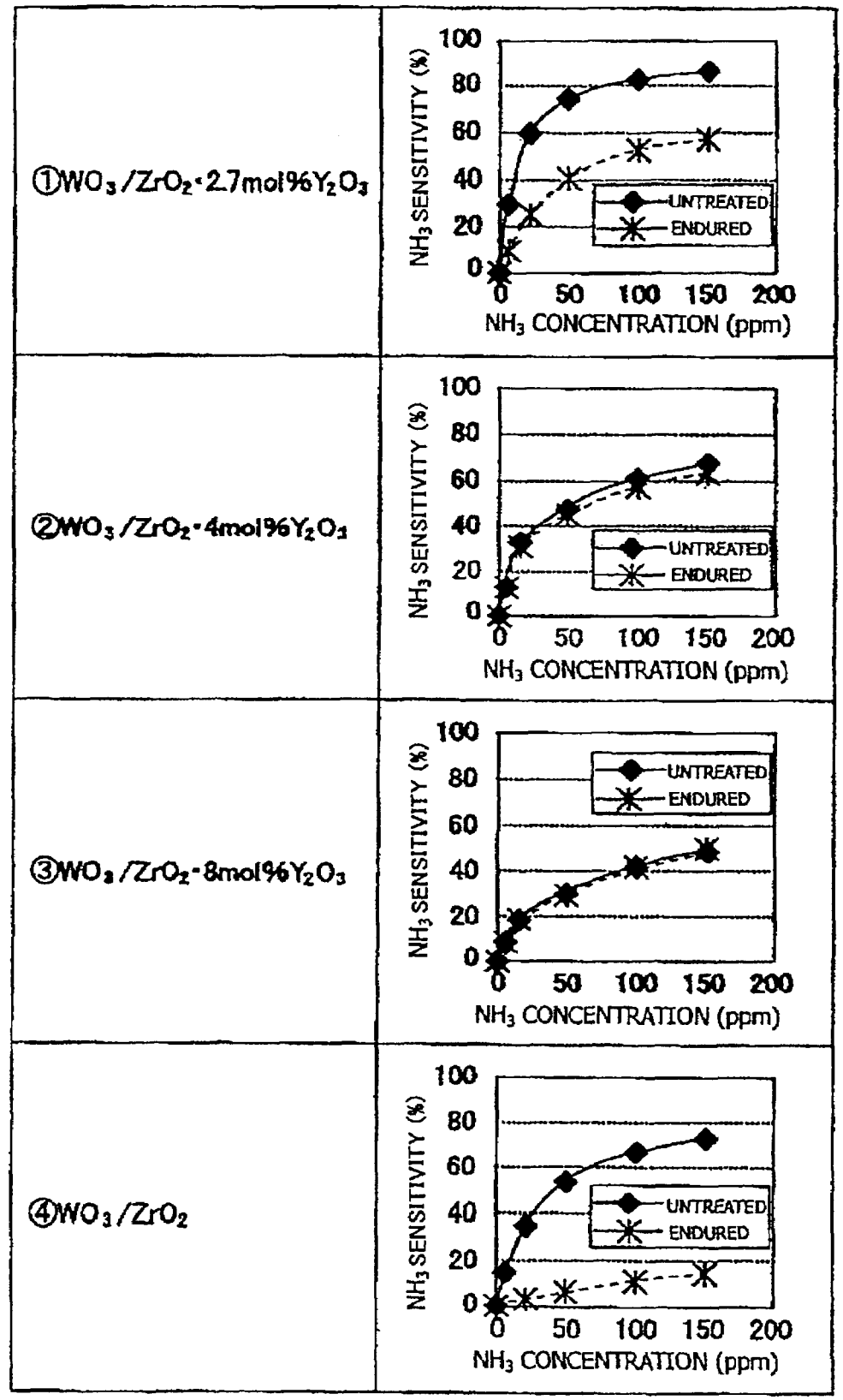

[FIG. 27]
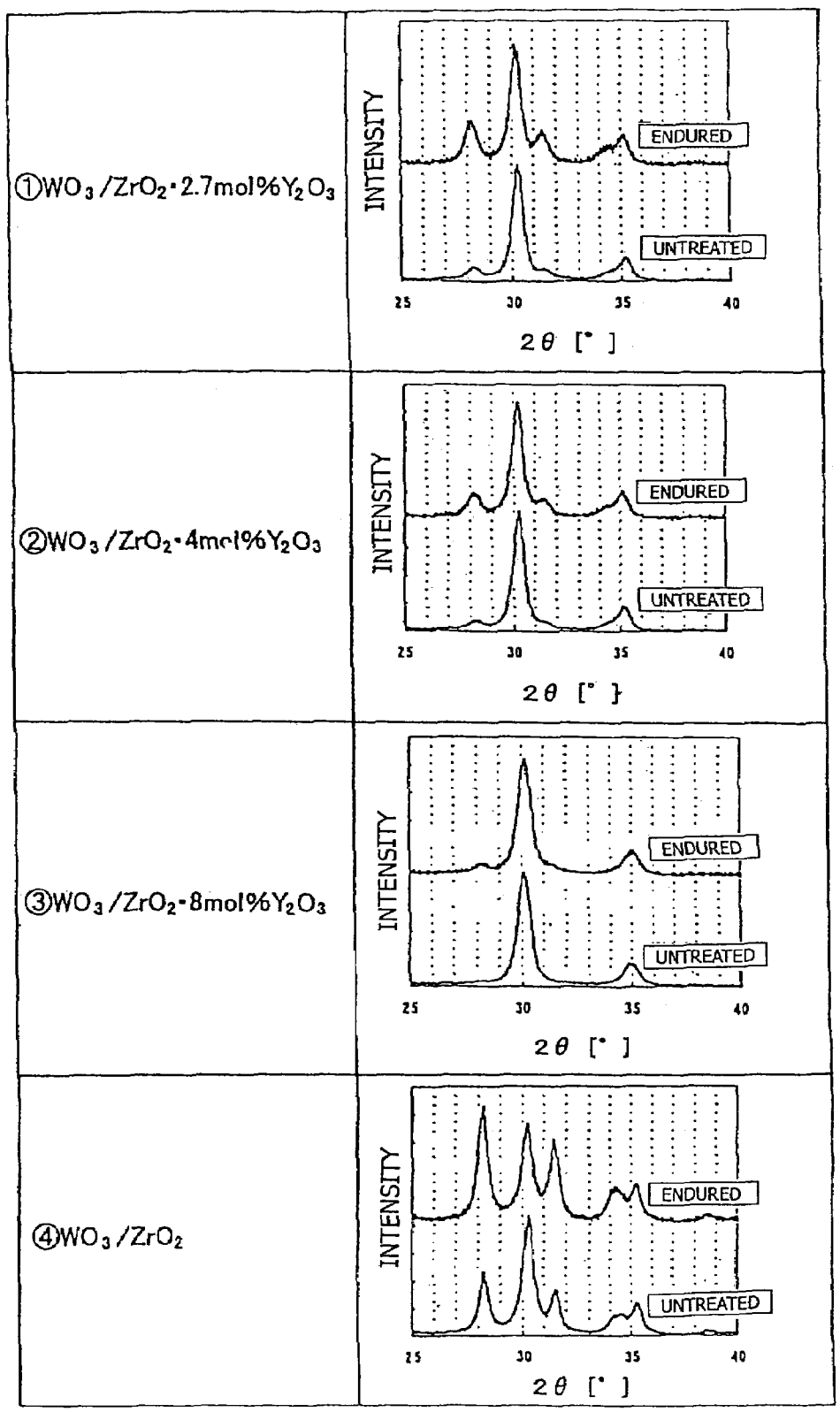

[FIG. 28]
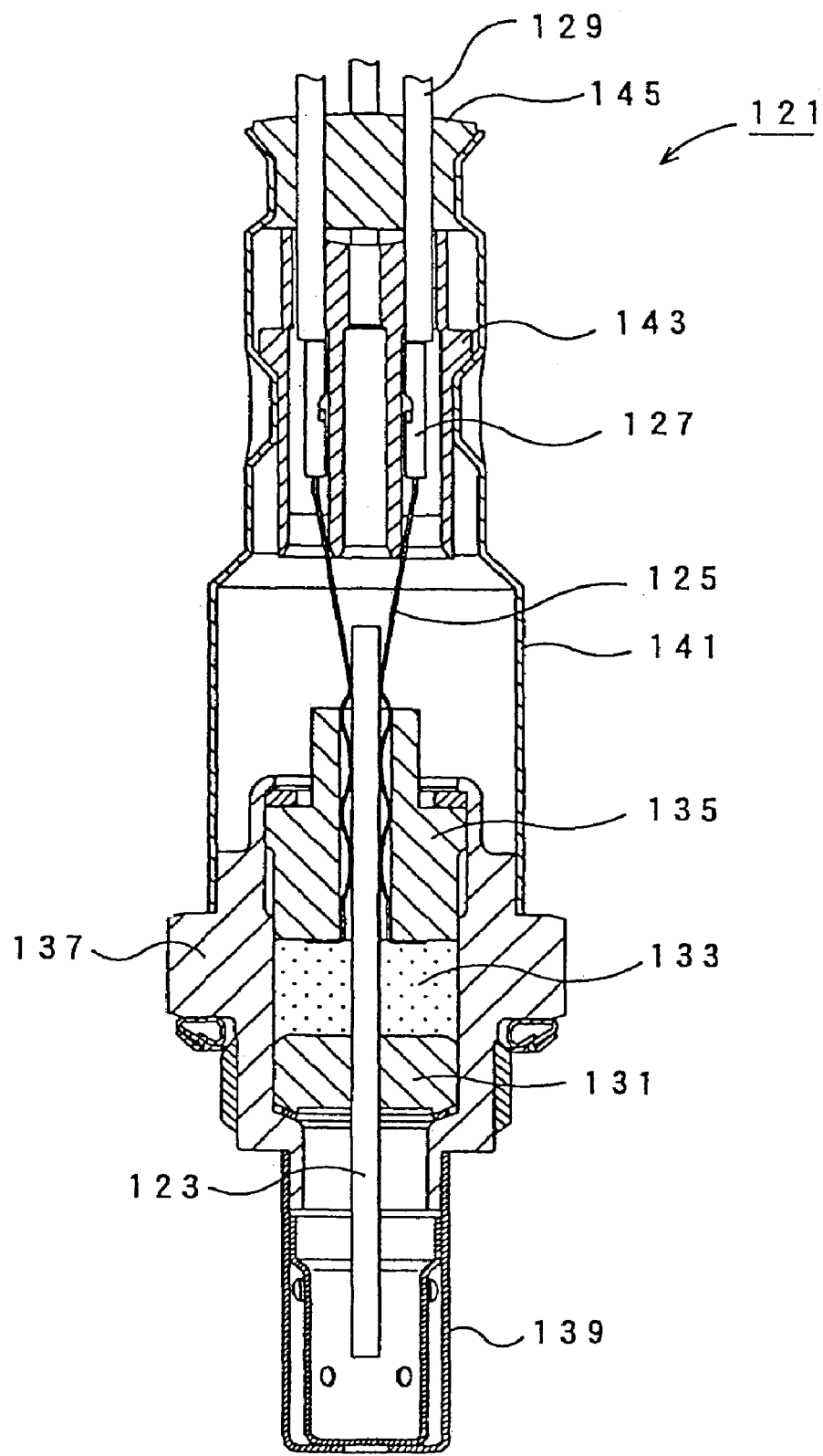

AMMONIA SENSOR

BACKGROUND OF THE INVENTION

1. Field of the Invention

The present invention relates to an ammonia sensor for detecting the concentration of ammonia contained in a sample gas. This type of ammonia sensor is employed for measuring the concentration of ammonia contained in, for example, exhaust gas from an internal combustion engine, and is particularly suitable for use in a system for selectively reducing $NO_x$ (hereinafter also referred to as an "$NO_x$ selective reduction system"), in which $NO_x$ is cleaned by addition of urea.

2. Description of the Related Art

In recent years, studies have been performed on cleaning of $NO_x$ discharged from an internal combustion engine. For example, in one technique (an $NO_x$ selective reduction system) that has been developed, urea is added to an SCR (selective catalytic reduction) catalyst to thereby generate ammonia, and $NO_x$ is chemically reduced by the thus-generated ammonia, to thereby clean the exhaust gas.

In this technique, in order to chemically reduce and clean discharged $NO_x$ by ammonia at high efficiency, the amount of urea to be added must be regulated, and thus the concentration of ammonia must be accurately measured.

In connection with this technique, for example, there have been disclosed an ammonia sensor incorporating a sensitive layer predominantly containing $WO_3$ and containing a noble metal (see, for example, Patent Document 1), and an ammonia sensor incorporating a sensitive layer predominantly containing $WO_3$ and containing $MoO_3$ (see, for example, Patent Document 2).

Meanwhile, ammonia sensors incorporating a sensitive layer formed of zeolite have been proposed (see Patent Documents 3 and 4).

Patent Document 1—Japanese Patent Application Laid-Open (kokai) No. 5-87760 (page 2)

Patent Document 2—Japanese Patent Application Laid-Open (kokai) No. 10-19821 (page 2)

Patent Document 3—Specification of U.S. Pat. No. 5,143,696 (page 3, FIG. 4)

Patent Document 4—Specification of U.S. Pat. No. 6,069,013 (page 3, FIG. 2a)

3. Problems to be Solved by the Invention

However, the ammonia sensor described in Patent Document 1 exhibits sensitivity to NO and $NO_2$, and thus cannot be employed in the $NO_x$ selective reduction system for chemical reduction and cleaning of $NO_x$ contained in exhaust gas by addition of urea.

The ammonia sensor described in Patent Document 2 exhibits improved selectivity for ammonia. However, $MoO_3$, which is incorporated into the sensitive layer for improving the ammonia selectivity of the sensor, has a melting point as low as 795° C. and a boiling point as low as 1,155° C. Therefore, the sensor is not suitable for use in the aforementioned $NO_x$ selective reduction system, because of its low thermal resistance. Thus, the sensor is difficult to employ in exhaust gas.

The ammonia sensor described in Patent Document 3 or 4 involves a problem in terms of thermal resistance. Specifically, a zeolite having a low $SiO_2/Al_2O_3$ ratio (i.e., the Al content is high), which is employed in the ammonia sensor, exhibits poor thermal resistance, and thus is not suitable as a material for, particularly, an exhaust gas sensor (see, for example, Society of Automotive Engineers of Japan, Inc., Academic Lecture Meeting Preprints 961 pp. 73-76).

In consideration of practical use of an ammonia sensor, a critical point is that the sensor must have durability (particularly, durability against heat). For example, even when the sensor is operated at a high temperature over a long period of time, the sensor must provide consistent output. However, in the aforementioned conventional sensors, considerations for enhancing durability have been insufficient.

SUMMARY OF THE INVENTION

The present invention has been achieved to solve the aforementioned problems, and an object of the invention is to provide an ammonia sensor exhibiting high sensitivity particularly to ammonia, high ammonia selectivity, and high thermal resistance and durability.

Another object of the present invention is to provide an ammonia sensor which measures the concentration of ammonia contained in a gas at high accuracy, even when the temperature of the gas is varied.

The present inventors have conducted studies for solving the aforementioned problems, and as a result have found that a solid, super-strong acidic substance is effective as a detection material (gas-sensitive material for a sensitive section) employed in an ammonia sensor. The present invention has been accomplished on the basis of this finding. The present invention will next be described in detail.

DETAILED DESCRIPTION OF THE INVENTION

As used herein, the term "super-strong acid" refers to an acid having an acidity of $\leq -11.93$ as determined by the Hammett acidity function $H_0$. Hammett acidity function $H_0$ is used for evaluating the ability of a solvent to donate a proton to a Hammett base B, and is represented by the following formula (2) for the relation expressed by the following formula (1).

[F1]

$$H^+ + B \leftrightarrows BH^+ \qquad (1)$$

$$H_0 = pKa + \log([B]/[BH^+]) \qquad (2)$$

As described below, the present invention provides an ammonia sensor including a sensitive section containing a primary component and a secondary component added thereto. Although the form of the secondary component present in the sensitive section has not necessarily been elucidated completely, and while not being bound by any theory, the present inventors consider that the primary component and the secondary component of the sensitive section exhibiting super-strong acidity are not present in the form of a mixture. Rather, the secondary component in molecular form is chemically bonded to the surfaces of oxide particles constituting the primary component.

For example, the described solid, super-strong acid (super-strong acidic metal oxide) described below is considered to have the structure shown in FIG. 1 (the upper figure and the middle figure) or a structure similar to the structure shown therein, in view of the results of studies employing XPS (X-ray photoelectron spectroscopy) and IR (infrared spectroscopy).

Also, the mechanism by which the sensitive section exhibits super-strong acidity when the secondary component is chemically bonded to the primary component, as described above, has not yet been completely elucidated. However, the mechanism is considered to be as shown in FIG. 1 (the lower structure).

Specifically, conceivably, when the secondary component is chemically bonded to the surfaces of the primary component particles, as shown by arrows in the lower structure of FIG. 1, the Lewis acidity of $Zr^{4+}$ is considerably increased by the inductive effect of the "S=O" double bond, whereby the sensitive section exhibits super-strong acidity.

In order to cause the sensitive section to exhibit super-strong acidity, as described above, the secondary component must be chemically bonded to the surfaces of the primary component particles. When the specific surface area of the primary component particles is larger, larger amounts of the secondary component molecules (particles) can be bonded to the surfaces of the primary component particles. As a result, the acid content of the sensitive section is increased.

Thus, the amount of the secondary component which can be added to the primary component varies in accordance with the specific surface area of the primary component. As described below, when the amount of the secondary component to be added is appropriately determined, the resultant ammonia sensor can reliably and selectively detect ammonia gas contained in a sample gas.

The present invention and various aspects and preferred optional features will next be described.

(1) The invention provides an ammonia sensor comprising an element section, the element section including a pair of electrodes and a sensitive section contacting the paired electrodes, characterized in that the sensitive section contains a solid, super-strong acidic substance other than a zeolite, the acidic substance having an acidity of $\leq -11.93$ as determined by Hammett acidity function $H_0$.

In the ammonia sensor (1) the sensitive section contains a solid, super-strong acidic substance other than a zeolite, the acidic substance having an acidity of $\leq -11.93$ as determined by Hammett acidity function $H_0$. Therefore, the ammonia sensor exhibits high sensitivity to ammonia, high ammonia selectivity, and high thermal resistance.

The reason why a solid, super-strong acidic substance other than a zeolite is employed in the sensitive section is that zeolite exhibits low thermal resistance. When the sensitive section predominantly contains the aforementioned solid, super-strong acidic substance (preferably, the entirety of the sensitive section is formed of the solid, super-strong acidic substance), the aforementioned characteristics of the ammonia sensor are further enhanced, which is more preferable. Specifically, the sensitive portion is operable when it contains at least 80% by weight of the super-strong acid substance.

(2) Preferably, the invention provides an ammonia sensor comprising an element section, the element section including a pair of electrodes, and a sensitive section contacting the paired electrodes, characterized in that the sensitive section contains a solid, super-strong acidic substance having an acidity of $\leq -11.93$ as determined by Hammett acidity function $H_0$; and the solid, super-strong acidic substance contains an oxide serving as a primary component and an oxide or an oxide ion serving as a secondary component, the primary and secondary components being chemically bonded to each other.

In the ammonia sensor (2), the sensitive section contains a solid, super-strong acidic substance having an acidity of $\leq -11.93$ as determined by Hammett acidity function $H_0$, and the primary component (an oxide) and the secondary component (an oxide or an oxide ion) of the solid, super-strong acidic substance are chemically bonded to each other. Therefore, the ammonia sensor exhibits high sensitivity to ammonia and high ammonia selectivity. In addition, because the primary component is an oxide and the secondary component is an oxide (or an oxide ion), the ammonia sensor exhibits high thermal resistance.

Chemical bonding between the primary component (an oxide) and the secondary component (an oxide or an oxide ion) can be confirmed, for example, by the following procedure: the sensitive section of the ammonia sensor is subjected to XPS measurement, to thereby obtain a specific electron orbital spectrum of the primary component (or the secondary component); and the thus-obtained spectrum is confirmed to have a peak that is shown in neither an electron orbital spectrum of merely the primary component (or merely the secondary component) nor an electron orbital spectrum of a mixture of the primary and secondary components.

The solid, super-strong acidic substance employed in this invention, in which the secondary component is bonded to the primary component, preferably has a specific surface area of about 35 to about 80 $m^2/g$. When the sensitive section predominantly contains the aforementioned solid, super-strong acidic substance (preferably, the entirety of the sensitive section is formed of the solid, super-strong acidic substance), the aforementioned characteristics of the ammonia sensor are further enhanced, which is more preferable.

(3) Preferably, the invention provides an ammonia sensor comprising an element section, the element section including a pair of electrodes, and a sensitive section contacting the paired electrodes, characterized in that the sensitive section contains a solid, super-strong acidic substance containing one oxide selected from among $Fe_2O_3$, $TiO_2$, $ZrO_2$, $HfO_2$, $SnO_2$, $Al_2O_3$, and $SiO_2$, serving as a primary component, and at least one species selected from among $WO_3$, $MoO_3$, $B_2O_3$, $SO_4^{2-}$ and $PO_4^{3-}$, serving as a secondary component.

In the ammonia sensor (3), the aforementioned solid, super-strong acidic substance (super-strong acidic metal oxide) is employed as the material of the sensitive section. Therefore, the ammonia sensor can accurately and selectively detect ammonia gas with high responsiveness and high sensitivity. When the sensitive section predominantly contains the aforementioned solid, super-strong acidic substance (preferably, the entirety of the sensitive section is formed of the solid, super-strong acidic substance), the aforementioned characteristics of the ammonia sensor are further enhanced, which is more preferable.

When the secondary component is $SO_4^{2-}$, the solid, super-strong acidic substance becomes a sulfated super-strong acidic metal oxide; and when the secondary component is $PO_4^{3-}$, the solid, super-strong acidic substance becomes a phosphorylated super-strong acidic metal oxide.

(4) Preferably, the invention is further characterized in that the solid, super-strong acidic substance is at least one species selected from among $WO_3/ZrO_2$, $SO_4^{2-}/ZrO_2$, $PO_4^{3-}/ZrO_2$, and $SO_4^{2-}/TiO_2$.

In aspect (4), the aforementioned solid, super-strong acidic substance is employed as the material of the sensitive section. Therefore, the ammonia sensor can accurately and selectively detect ammonia gas with high responsiveness and high sensitivity.

(5) Preferably, the invention is further characterized in that the solid, super-strong acidic substance is a composite oxide containing a $ZrO_2$ carrier serving as a primary component, and at least one species selected from among $WO_3$, $MoO_3$, $B_2O_3$, $SO_4^{2-}$ and $PO_4^{3-}$, serving as a secondary component, the secondary component being bonded to the surface of the carrier; and the carrier contains an agent for stabilizing the crystal structure of $ZrO_2$.

In aspect (5), the $ZrO_2$ carrier serving as the primary component contains an agent for stabilizing the $ZrO_2$ crystal structure. Therefore, the ammonia sensor exhibits excellent thermal resistance and durability against heat. Even when the ammonia sensor is employed at a high temperature (e.g., 400° C. or higher) over a long period of time, the sensor exhibits a remarkable effect; i.e., the sensor provides consistent output.

In aspect (5), a predetermined amount of a crystal-structure-stabilizing agent is incorporated into the $ZrO_2$ carrier (specifically to form a solid solution) so as to stabilize a $ZrO_2$ crystal phase, whereby change in the crystal structure of $ZrO_2$ by heat can be suppressed. Therefore, since the secondary component is reliably bonded to the surface of the carrier, even when the ammonia sensor is employed at a high temperature over a long period of time, the sensitivity of the sensor is not lowered, and the sensor provides consistent output.

The crystal structure in relation to the invention of aspect (5) will now be described.

The present inventors have performed studies on durability of an ammonia sensor, and have found that the sensitivity of the ammonia sensor is gradually lowered as the service time progresses, and, in accordance with lowering of the sensitivity, the proportion of monoclinic crystals is increased in the $ZrO_2$ crystal phase.

The present inventors have also found that when a stabilizing agent (e.g., $Y_2O_3$) is added to $ZrO_2$ serving as the primary component, to thereby cause $ZrO_2$ to have a crystal phase containing tetragonal crystals and cubic crystals and not containing monoclinic crystals, the durability of the ammonia sensor is enhanced, and lowering of the sensitivity of the sensor is significantly retarded. The invention of aspect (5) has been accomplished on the basis of this finding.

(6) Preferably, the invention is further characterized in that the crystal-structure-stabilizing agent is at least one species selected from among CaO, MgO, $Y_2O_3$, $Yb_2O_3$, and $Ga_2O_3$.

The invention of aspect (6) specifies certain species of the stabilizing agent.

(7) Preferably, the invention is further characterized in that the $Y_2O_3$ content is at least 4 mol %.

In the case where $Y_2O_3$ is added in an amount of 4 mol % or more, even when the ammonia sensor is employed at a high temperature, change in the $ZrO_2$ crystal phase is considerably suppressed, and therefore lowering of the sensitivity of the sensor can be effectively prevented.

(8) Preferably, the invention is further characterized in that the $Y_2O_3$ content is at least 6 mol %.

In the case where the $Y_2O_3$ content of the $Y_2O_3$-containing $ZrO_2$ carrier serving as the primary component is 6 mol % or more (preferably 8 mol % or more) on the basis of the entire amount (100 mol %) of the carrier, even when the ammonia sensor is employed at a high temperature, change in the $ZrO_2$ crystal phase is suppressed considerably, thereby further preventing lowering of the sensitivity of the sensor.

When $Y_2O_3$ is added to $ZrO_2$ in an amount of about 4 to about 6 mol %, the stability of the $ZrO_2$ crystal phase is enhanced, and the resultant $ZrO_2$ is called "partially stabilized zirconia." When $Y_2O_3$ is added to $ZrO_2$ in an amount of more than 6 mol %, the stability of the crystal phase of $ZrO_2$ is further enhanced, and the resultant $ZrO_2$ is called "completely stabilized zirconia."

(9) Preferably, the invention is further characterized in that the solid, super-strong acidic substance has an acid content of at least 0.05 mmol/g.

In aspect (9), a preferred acid content of the solid, super-strong acidic substance is specified. When the acid content falls within the above range, the ammonia sensor adsorbs a sufficient amount of ammonia, and the sensor exhibits satisfactory performance. The acid content more preferably falls within a range of 0.07 to 0.25 mmol/g.

When the acid content is higher, the ammonia sensor exhibits more enhanced sensitivity to ammonia gas. Therefore, the operation temperature of the sensor element can be increased.

When the operation temperature of an ammonia sensor is increased, the sensitivity of the sensor tends to be lowered. An ammonia sensor employing a solid, super-strong acidic substance having a high acid content maintains sufficient sensitivity even when operated at a high temperature. In addition, when the sensor is operated at a high temperature, the sensor advantageously exhibits quick responsiveness.

The acid content can be calculated from the integral (area) of the peak obtained by means of the $NH_3$-TPD (ammonia-temperature programmed desorption) technique described below.

(10) Preferably, the invention is further characterized in that when the total amount of the aforementioned primary and secondary components is taken as 100 mol %, the amount of the secondary component is 1 to 25 mol %; i.e., the amount of the primary component is 99 to 75 mol %.

In aspect (10), the amount of the secondary component to be added is specified. When the amount of the secondary component falls within the above range, the ammonia sensor can reliably and selectively detect ammonia gas contained in a sample gas, which is preferable.

Particularly when the amount of the secondary component is 2.7 to 18.6 mol %; i.e., when the amount of the primary component is 97.3 to 81.4 mol %, the ammonia sensor exhibits enhanced sensitivity to ammonia, which is more preferable.

In consideration of the aforementioned range of the amount (mol %) of the primary component, the specific surface area of particles of the primary component is preferably about 100 $m^2/g$.

(11) Preferably, the invention is further characterized in that, when the sensitive section predominantly contains $ZrO_2$ and contains at least W, the W content of the sensitive section is 1.5 to 30 wt. % as reduced to $WO_3$.

In aspect (11), the sensitive section predominantly contains $ZrO_2$, and therefore exhibits high thermal resistance. Since the sensitive section predominantly contains $ZrO_2$ and contains at least W, the ammonia sensor exhibits high sensitivity to ammonia and low sensitivity to gases other than ammonia (i.e., interference gases such as NO and $NO_2$); i.e., the sensor exhibits high selectivity for ammonia.

As specified in the invention of aspect (11), when the amount of W contained in the sensitive section is 1.5 to 30 wt. % as reduced to $WO_3$, the ammonia sensor exhibits high sensitivity to ammonia.

In aspect (11), the amount of W contained in the raw material of the sensitive section (the amount of W incorporated into the raw material) is 2 to 40 wt. % as reduced to $WO_3$.

(12) Preferably, the invention is further characterized in that the ammonia sensor comprises a protective layer which covers the sensitive section.

In aspect (12), the surface of the sensitive section is covered with a protective layer which $NH_3$ can permeate (e.g., a porous protective layer). Therefore, adhesion to the sensitive section of a deposit (e.g., carbon) contained in exhaust gas or a poisoning substance (e.g., phosphorus or silicon) contained in exhaust gas can be prevented, and thus impairment of the sensitive section can be suppressed.

Examples of the dominant material constituting the protective layer include magnesia-alumina spinel, alumina, zirconia, and titania.

(13) Preferably, the invention is further characterized in that the ammonia sensor further comprises a heater for heating the element section.

In aspect (13), the element section is heated by the heater, to thereby regulate the temperature of the element section (particularly, the temperature of the sensitive section) to an optimal temperature for detection of ammonia. This regulation of the temperature of the element section advantageously enhances sensor performance, including responsiveness and accuracy in measurement of ammonia concentration.

(14) Preferably, the invention is further characterized in that the ammonia sensor comprises an insulating substrate in which the heater is embedded, wherein the paired electrodes are formed on the insulating substrate, and the sensitive section is formed so as to cover the paired electrodes.

In aspect (14), a specific configuration of the element section is described. The ammonia sensor having the aforementioned configuration is preferred, since the sensor is readily produced and is suitable for mass-production, and exhibits high mechanical strength. The paired electrodes may be parallel electrodes or comb-shaped electrodes.

(15) Preferably, the invention is further characterized in that the ammonia sensor comprises an insulating substrate in which the heater is embedded, a lower electrode, and an upper electrode, the lower and upper electrodes being formed of the paired electrodes, wherein the lower electrode is formed on the insulating substrate, the sensitive section is formed so as to cover the lower electrode, and the upper electrode is formed on the sensitive section.

In aspect (15), a specific configuration of the element section is described. The ammonia sensor having the aforementioned configuration is preferred, since the sensor is readily produced and is suitable for mass-production, and exhibits high mechanical strength. In addition, the upper electrode may serve as a protective layer for the sensitive section.

(16) Preferably, the invention is further characterized in that the ammonia sensor further comprises element temperature detection means for detecting the temperature of the element, and temperature regulation means for controlling the heater such that the element temperature falls within a predetermined temperature range.

In aspect (16), the element temperature detection means detects the element temperature (the temperature of the element section), to thereby regulate, for example, voltage applied to the heater such that the element temperature falls within a predetermined temperature range (a temperature range suitable for measurement of the concentration of ammonia). Therefore, the ammonia sensor can consistently measure the concentration of ammonia with high accuracy.

The sensitivity of the ammonia sensor to ammonia varies depending on the element temperature. Therefore, when the element temperature is regulated to a predetermined temperature, the concentration of ammonia can be accurately measured. The element temperature can be regulated in accordance with the environment in which ammonia is measured. For example, in order to accurately measure the concentration of ammonia contained in exhaust gas from a diesel engine, preferably, the ammonia sensor is operated such that the element section is maintained at a predetermined temperature of about 350 to about 450° C., in consideration of the temperature of the exhaust gas, which varies in accordance with the operational conditions of the diesel engine.

The responsiveness (response speed) of the ammonia sensor to ammonia depends on the operation temperature of the sensor (the heating temperature of the element section). The higher the operation temperature, the higher the rate at which ammonia gas molecules are adsorbed onto or desorbed from the sensor, and thus the more enhanced the responsiveness of the sensor to ammonia. Meanwhile, when the operation temperature of the ammonia sensor is increased, the sensitivity of the sensor to ammonia gas is lowered.

In view of the foregoing, preferably, the temperature of the element section (t° C.) is regulated to a predetermined temperature falling within a range represented by the following relation: $T-100 \leq t \leq T+100$ (wherein T represents the peak end temperature (° C.) as measured by means of $NH_3$-TPD).

The element temperature detection means may be a temperature sensor formed of a platinum resistor or a thermistor.

BRIEF DESCRIPTION OF THE DRAWINGS

FIG. 1 is an explanatory view showing the structures of solid, super-strong acidic substances.

FIG. 2 is a perspective view of the entirety of the element section of the ammonia sensor of the first embodiment, and exploded perspective view of the element section.

FIG. 3 is a cross-sectional view of the element section shown in FIG. 2, as taken along line A-A'.

FIG. 4 is a cross-sectional view of the entire configuration of the ammonia sensor of the first embodiment.

FIG. 5 is an explanatory view showing the method for using the ammonia sensor.

FIG. 6 is a graph showing the relationship between $NH_3$ concentration and impedance as obtained in Test Example 1.

FIG. 7 is a graph showing the relationship between $NH_3$ concentration and impedance as obtained in Test Example 1.

FIG. 8 is a graph showing the relationship between $NH_3$ concentration and impedance as obtained in Test Example 1.

FIG. 9 is a graph showing the relationship between $NH_3$ concentration and impedance as obtained in Test Example 1.

FIG. 10 is a graph showing the relationship between $NH_3$ concentration and impedance as obtained in Test Example 1.

FIG. 11 is a graph showing the relationship between $NH_3$ concentration and impedance as obtained in Test Example 1.

FIG. 12 is a graph showing the relationship between $NH_3$ concentration and impedance as obtained in Test Example 1.

FIG. 13 is a graph showing the relationship between $NH_3$ concentration and impedance as obtained in Test Example 1.

FIG. 14 is a graph showing the relationship between $NH_3$ concentration and impedance as obtained in Test Example 1.

FIG. 15 is a graph showing the relationship between $NH_3$ concentration and impedance as obtained in Test Example 1.

FIG. 16 is a graph showing the relationship between $NH_3$ concentration and impedance as obtained in Test Example 1.

FIG. 17 is a graph showing the selectivity of the ammonia sensor of Test Example 2.

FIG. 18 is a graph showing the selectivity of the ammonia sensor of Test Example 2.

FIG. 19 is a graph related to Test Example 3, showing the gas temperature dependency of $NH_3$ sensitivity in the case where element temperature is not regulated.

FIG. 20 is a graph related to Test Example 3, showing the gas temperature dependency of $NH_3$ sensitivity in the case where element temperature is regulated.

FIG. 21 is a graph showing the results of $NH_3$-TPD measurement of the sensitive layer.

FIG. 22 is a graph showing the relationship between the element temperature and the responsiveness to $NH_3$ gas, as obtained in Test Example 4.

FIG. 23 is a graph showing the relationship between the element temperature and the responsiveness to $NH_3$ gas, as obtained in Test Example 4.

FIG. 24 is a perspective view of the entirety of the element section of the ammonia sensor of the second embodiment, and exploded perspective view of the element section.

FIG. 25 is a cross-sectional view of the element section shown in FIG. 24, as taken along line B-B'.

FIG. 26 is a graph showing the results of a thermal durability test performed in Test Example 5.

FIG. 27 is a graph showing characteristics of the crystal structure as confirmed in the thermal durability test performed in Test Example 6.

FIG. 28 is a cross-sectional view of the entire configuration of the ammonia sensor of the fourth embodiment.

Reference numerals used to identify certain elements of the drawings are described as follows.

1, 101, 121: ammonia sensor
3, 103: element section
5, 105: insulating substrate
6, 102, 123: sensor element member
7, 9, 107, 109: lead portion
11, 13: comb-shaped electrode
15, 115: sensitive layer
17, 117: protective layer
19, 119: heater
21, 120: temperature sensor
111: lower electrode
115: upper electrode

DETAILED DESCRIPTION OF THE INVENTION

Next, the present invention (embodiments of the ammonia sensor of the present invention) will be described in greater detail by reference to the drawings which should not be construed as limiting the invention in any way.

First Embodiment a) The configuration of the ammonia sensor of the present embodiment will now be described. FIG. 2 is a perspective view of an essential portion of the ammonia sensor and an exploded perspective view of the essential portion. FIG. 3 is a cross-sectional view of the essential portion shown in FIG. 2, as taken along line A-A'.

As shown in FIG. 2, the ammonia sensor 1 of the present embodiment employs a gas-sensitive material whose impedance (Z) varies in accordance with the concentration of ammonia. When alternating voltage is applied to the ammonia sensor of the present embodiment, the impedance (Z) of the gas-sensitive material varies in accordance with the concentration of ammonia. Therefore, the ammonia concentration is determined on the basis of variation in impedance.

An element section 3 constituting the essential portion of the ammonia sensor 1 includes an insulating substrate 5 and the below-described components successively laminated thereon. Hereinafter, the insulating substrate 5 having the laminated components may be referred to as "sensor element member 6." FIG. 2 shows merely the front-end portion of the sensor element member 6.

Specifically, a pair of lead portions 7 and 9 which predominantly contain platinum are provided on the insulating substrate 5 formed of alumina; a pair of comb-shaped electrodes 11 and 13 are connected to the lead portions 7 and 9, respectively; a sensitive layer 15 (sensitive section) formed of the aforementioned gas-sensitive material is provided on the comb-shaped electrodes 11 and 13 so as to cover the entirety of the electrodes 11 and 13; and a protective layer 17 is provided on the sensitive layer 15 so as to cover the entirety of the layer 15.

As shown in FIG. 3, a heater 19 for heating the element section 3 and a temperature sensor 21, which is a temperature-measuring resistor, are provided in the interior of the insulating substrate 5. The heater 19 predominantly contains platinum, and the temperature sensor 21 also predominantly contains platinum.

The sensitive layer 15 (thickness: about 30 µm) formed by thick-film printing contains a porous gas-sensitive material (i.e., a solid, super-strong acidic substance). The impedance (or resistance) of the solid, super-strong acidic substance varies in accordance with variation in the concentration of ammonia contained in an atmosphere surrounding the substance.

Specifically, the sensitive layer 15 contains, as a primary component, an oxide selected from $Fe_2O_3$, $TiO_2$, $ZrO_2$, $HfO_2$, $SnO_2$, $Al_2O_3$, $SiO_2$, etc. in an amount of 99 to 75 mol %, and contains, as a secondary component, at least a species selected from among $SO_4^{2-}$, $PO_4^{3-}$, $WO_3$, $MoO_3$, $B_2O_3$, etc. in an amount of 1 to 25 mol %.

The amount of the primary and secondary components of the sensitive layer 15 can be obtained, for example, by the following procedure: the amount of the elements constituting the components is determined by use of an inductively coupled argon plasma emission spectrophotometer (IRIS Advantage ICAP, product of Nippon Jarrell-Ash Co., Ltd.); and, on the basis of the thus-determined amount of the elements, the amount of the corresponding oxides is calculated, to thereby obtain the amount of the primary and secondary components.

The protective layer 17 (thickness: about 30 µm) formed through thick-film printing prevents adhesion of a deposit (e.g., carbon) to the comb-shaped electrodes 11 and 13 or the sensitive layer 15. The protective layer 17 is formed of a porous protective film predominantly containing magnesia-alumina spinel ($MgAl_2O_4$).

The entire configuration of the ammonia sensor 1, which is an assembly incorporating the aforementioned sensor element member 6, will now be described briefly.

As shown in FIG. 4, in the ammonia sensor 1, the sensor element member 6—which, at its front-end portion (the lower portion as viewed in FIG. 4), includes the element section 3—is connected to lead wires 31 at the rear-end portion (the upper portion as viewed in FIG. 4). The lead wires 31 are welded to first ends of electrode leads 33. A second end of each of the electrode leads 33 is connected via a connection terminal 35 to a lead wire 37.

The rear-end portion of the sensor element member 6 is accommodated in an alumina tubular insulator 39, and the front-end portion of the member 6 projects from the insulator 39. Specifically, at the lower end portion of the insulator 39, the sensor element member 6 is fitted into an alumina insulating porcelain bushing 41 which is provided in the interior of the insulator 39, and is connected to the insulating porcelain bushing 41 by use of cement 43. The insulator 39 and the sensor element member 6 are fixed together via a first filler layer 45 and a second filler layer 47, the layers 45 and 47 being formed by melting and solidification of a powder mixture of talc and glass. A portion at which the lead wires 31 are connected to the electrode leads 33 is encapsulated with a glass layer 49 formed by melting and solidifying a glass powder.

The front-end portion of the sensor element member 6 is protected by a porous protector 53 which is supported by a main fitting 51. The insulator 39 is fitted in the main fitting 51 via a packing plate 55 and a talc layer 57. A crimping ring 59 for sealing the talc layer 57 is provided around the insulator 39, an outer tube 61 is provided around the crimping ring 59, and a ring 63 is provided around a first end of the outer tube 61. The upper end portion of the main fitting 51 is crimped so as to cover the ring 63.

A protective outer tube 65 is joined to a second end of the outer tube 61 by crimping, and the connection terminal 35 and the lead wire 37 are supported by a rubber cap 67 fitted in the protective outer tube 65.

b) Next, the method for producing the ammonia sensor 1 of the present embodiment (particularly, the sensor element member 6) will be described.

1) Firstly, the lead portions 7 and 9 and the comb-shaped electrodes 11 and 13 are formed on the insulating substrate 5.

Specifically, in order to form the lead portions 7 and 9 on the insulating substrate 5 formed of $Al_2O_3$, a Pt-containing paste is applied by printing onto the substrate 5, dried at 120° C. for one hour, and fired at 1,400° C. for one hour.

In order to form the comb-shaped electrodes 11 and 13, by use of a mask (not illustrated) having an opening whose shape corresponds to the shape of the electrodes 11 and 13, an Au paste is applied by printing such that end portions of the lead portions 7 and 9 overlap with the corresponding end portions of the comb-shaped electrodes 11 and 13, dried at 120° C. for one hour, and fired at 1,000° C. for one hour.

2) Subsequently, the sensitive layer 15 is formed from a material produced by the below-described synthesis method A such that the layer 15 covers the comb-shaped electrodes 11 and 13.

Specifically, zirconium oxynitrate is dissolved in $H_2O$, and aqueous ammonia is added to the resultant solution, to thereby adjust the pH of the solution to 8. The thus-obtained zirconium hydroxide is subjected to suction filtration, followed by washing. Thereafter, the resultant zirconium hydroxide is dried in a drying machine at 110° C. for 24 hours, and then fired in an electric furnace at 400° C. for 24 hours, to thereby yield a $ZrO_2$ powder having a large surface area.

Separately, ammonium tungstate is dissolved in $H_2O$, and aqueous ammonia is added to the resultant solution, to thereby prepare a solution (W solution) having a pH of 10 to 11.

The above-obtained $ZrO_2$ powder is mixed with the W solution such that the amount of W as reduced to $WO_3$ becomes a predetermined value of 2 to 40 wt. % on the basis of the total amount (100 wt. %) of $WO_3$ and $ZrO_2$, and the resultant mixture is placed in a crucible. Thereafter, the mixture is dried in a drying machine at 120° C. for 24 hours, and then fired in an electric furnace at 800° C. for five hours, to thereby yield a W-containing $ZrO_2$ powder (the target material).

Subsequently, the above-obtained W-containing $ZrO_2$ powder (i.e., powder containing a primary component and a secondary component), an organic solvent, and a dispersant are placed in a mortar, and disperse-mixed by use of a smash-mixing machine for four hours. Thereafter, a binder is added to the resultant mixture, and wet-mixed for four hours, to thereby prepare a slurry. The viscosity of the resultant slurry is regulated, to thereby yield a paste.

The thus-obtained paste containing the gas-sensitive material is applied by screen printing onto the insulating substrate 5 having the printed comb-shaped electrodes 11 and 13, so as to form a thick film. Thereafter, the paste is dried at 60° C., and then baked on the insulating substrate 5 by firing for one hour at 600° C.

3) Subsequently, the protective layer 17 is formed on the sensitive layer 15.

Specifically, a spinel ($MgAl_2O_4$) paste is applied onto the sensitive layer 15 by printing.

Thus, the sensor element member 6 of the ammonia sensor 1 of the present embodiment is produced.

c) The method for using the ammonia sensor 1 will next be described briefly.

The ammonia sensor 1 of the present embodiment is employed in a system for reducing the amount of $NO_x$ contained in exhaust gas from a vehicle (diesel vehicle).

In this system, specifically, as shown in FIG. 5, urea serving as a reducing agent is supplied to a known SCR catalytic system 75 provided on the upstream side of an oxidation catalyst 73 mounted on an exhaust pipe 71 of a vehicle, to thereby generate ammonia, and $NO_x$ contained in exhaust gas is chemically reduced to nitrogen by the thus-generated ammonia, to thereby clean the exhaust gas.

In order to efficiently reduce and clean the exhaust gas, the amount of urea to be supplied (i.e., the concentration of ammonia to be generated) must be regulated. Therefore, the ammonia sensor 1 is provided downstream of the SCR catalytic system 75, to thereby determine the concentration of ammonia discharged from the SCR catalytic system 75.

When the ammonia concentration is equal to or lower than the detection limit of the ammonia sensor 1, the supply amount of urea is increased, whereas when ammonia is detected by the ammonia sensor 1, the supply amount of urea is decreased in accordance with the thus-determined ammonia concentration. Through such regulation of the urea supply amount, the exhaust gas can be chemically reduced and cleaned at high efficiency.

When the ammonia sensor 1 of the present embodiment is not employed for measuring the concentration of ammonia, the ammonia sensor 1 can be cleaned by heating, to thereby maintain the performance of the ammonia sensor 1 at a high level.

Specifically, during the course of operation of an internal combustion engine, electricity is applied to the heater 19 such that the element section 3 is heated at, for example, a temperature of 500 to 700° C. (i.e., a temperature higher than the element temperature when the ammonia sensor 1 is employed in a routine manner and a temperature lower than the calcining temperature required for obtaining the powdery material of the sensitive layer 15); for example, the element section 3 is heated at 600° C. for five minutes. By such heat treatment, a substance adsorbed onto the ammonia sensor 1 (particularly, the sensitive layer 15), such as moisture or miscellaneous gases, can be completely removed.

Thus, the characteristics of the ammonia sensor 1 can be restored.

The aforementioned $NH_3$ concentration measurement and heat cleaning are controlled by a non-illustrated electronic control apparatus (e.g., a microcomputer).

d) TEST EXAMPLES

Next, Test Examples 1 through 4 will be described in which the effects of the ammonia sensor of the present embodiment were confirmed. Samples, a test apparatus, etc., employed in the Test Examples will now be described.

1) Ammonia Sensor

In the present Test Examples, ammonia sensors were produced (sample Nos. 1 through 10), each including the corresponding sensitive layer shown in Table 1, the sensitive layer being formed from a material produced by any of the below-described production methods.

Specifically, ammonia sensors (sample Nos. 1 through 4) were produced, each including a sensitive layer formed from a material produced by the production method described in the first embodiment (synthesis method A).

Also, an ammonia sensor (sample No. 5) was produced, including a sensitive layer formed from a material produced by the below-described synthesis method B.

In synthesis method B, firstly, a zirconium nitrate aqueous solution is added dropwise to aqueous ammonia, and the thus-prepared zirconium hydroxide precipitate is washed with water and then stirred in an ammonium tungstate aqueous solution. Subsequently, the resultant precipitate is filtered, and dried in a drying machine at 110° C. for 12 hours. The thus-dried precipitate is fired at 700° C. for five hours, to thereby yield a W-containing $ZrO_2$ powder (the target material). In a manner similar to that of the first embodiment, an ammonia sensor including a sensitive layer formed from the W-containing $ZrO_2$ powder was produced.

Furthermore, ammonia sensors (sample Nos. 7 through 9) were produced, each including a sensitive layer formed from a material produced by the below-described synthesis method C.

Specifically, in the case of production of an ammonia sensor (sample No. 8), a zirconium nitrate aqueous solution is added dropwise to aqueous ammonia, and the thus-prepared zirconium hydroxide precipitate is washed with water and then stirred in a 0.5 M sulfuric acid aqueous solution. Subsequently, the resultant precipitate is filtered and dried in a drying machine at 100° C. for 12 hours. The thus-dried precipitate is fired at 650° C. for five hours, to thereby yield an S-containing $ZrO_2$ powder (the target material). In a manner similar to that of the first embodiment, an ammonia sensor including a sensitive layer formed from the S-containing $ZrO_2$ powder was produced.

In the case of production of an ammonia sensor (sample No. 7), titanium chloride was employed in place of a zirconium nitrate aqueous solution, and the resultant precipitate was fired at 525° C. for five hours, to thereby synthesize the target material. In the case of production of an ammonia sensor (sample No. 9), a phosphoric acid aqueous solution was employed in place of a sulfuric acid aqueous solution, and the resultant precipitate was fired at 650° C. for five hours, to thereby yield the target material.

Meanwhile, a comparative ammonia sensor (sample No. 6) including a sensitive layer containing merely a primary component, and a comparative ammonia sensor (sample No. 10) including a sensitive layer containing merely a secondary component were produced. Each of the sensitive layers was formed as follows: a paste was prepared from a powder containing a single component (primary component or secondary component), and the paste was baked on the substrate, to thereby form the sensitive layer.

2) Evaluation Apparatus (Gas Measuring Apparatus)

In the below-described Test Examples 1 through 4, a sample gas generation apparatus was employed for evaluating the above-produced ammonia sensors. Each of the ammonia sensors was evaluated under the following measurement conditions.

<Measurement Conditions>
Gas temperature: 280° C., 300° C., 400° C.
Element temperature: 350° C., 400° C., 450° C.
Gas composition: $O_2$: 10 vol. %, $CO_2$: 5 vol. %,
$H_2O$: 5 vol. %, $NH_3$: 0 to 200 ppm,
$N_2$: balance
Interference gases: $NO_2$, NO, CO, $C_3H_6$: 100 ppm each ($C_3H_6$: 100 ppmC)

The ammonia sensor to be tested was placed in the evaluation apparatus and exposed to the gas flowing through the apparatus, an AC voltage (2 V) of a predetermined frequency (400 Hz) was applied between the electrode leads of the ammonia sensor, and the impedance of the ammonia sensor (i.e., the sensitive layer) was determined from the value of current flowing between the electrode leads.

The sensitivity of the ammonia sensor to $NH_3$ is expressed, in this embodiment, by the following equation; $NH_3$ sensitivity$=(Z_{base}-Z_{NH3})/Z_{base} \times 100[\%]$, wherein $Z_{base}$ is an impedance of the sensor as measured when the gas contains 0 ppm of $NH_3$ and $Z_{NH3}$ is an impedance of the sensor as measured when the gas contains $NH_3$. The equation is similarly applied to the sensitivity to any other gas component.

The Test Examples will next be described in detail.

In the present Test Examples, the specific surface area of each of the solid, super-strong acidic substances containing the corresponding primary and secondary components shown in Table 1, the sensitivity of the ammonia sensor to $NH_3$, and the acid content of the acidic substance were evaluated. The results are shown in Table 2.

The "Analytical value" shown in Table 1 refers to a value obtained by analyzing the sensitive layer of the above-produced ammonia sensor using the aforementioned inductively coupled argon plasma emission spectrophotometer.

The acidity of each of the acidic substances as determined by Hammett acidity function $H_0$ was measured by use of a Hammett indicator by means of the method described in "ADVANCES IN CATALYSIS VOLUME 37 (ACADEMIC PRESS, INC) pp. 186-187."

TABLE 1

| | Composition of sensitive layer | | | | | | |
|---|---|---|---|---|---|---|---|
| | | | Raw material | | Analytical value | Hammett | |
| Sample No. | Primary component | Secondary component | Mol ratio (primary:secondary) | Weight ratio (primary:secondary) | Mol ratio (primary:secondary) | acidity function $H_0$ | Synthesis method |
| 1 | $ZrO_2$ | $WO_3$ | 98.93:1.07 | 98.0:2.0 | 98.86:1.14 | −14.52 | A |
| 2 | $ZrO_2$ | $WO_3$ | 97.28:2.72 | 95.0:5.0 | 97.11:2.89 | −14.52 | A |

TABLE 1-continued

| | | | Composition of sensitive layer | | | | |
|---|---|---|---|---|---|---|---|
| | | | Raw material | | Analytical value | Hammett | |
| Sample No. | Primary component | Secondary component | Mol ratio (primary:secondary) | Weight ratio (primary:secondary) | Mol ratio (primary:secondary) | acidity function $H_0$ | Synthesis method |
| 3 | $ZrO_2$ | $WO_3$ | 94.42:5.58 | 90.0:10.0 | 94.83:5.17 | −14.52 | A |
| 4 | $ZrO_2$ | $WO_3$ | 91.43:8.57 | 85.0:15.0 | 92.52:7.48 | −14.52 | A |
| 5 | $ZrO_2$ | $WO_3$ | 82.52:17.48 | 71.5:28.5 | 82.52:17.48 | −14.52 | B |
| 6 | $ZrO_2$ | — | 100:0 | — | 100:0 | — | A |
| 7 | $TiO_2$ | $SO_4^{2-}$ | 96.74:3.26 | 96.1:3.9 | 96.74:3.26 | −13.75 | C |
| 8 | $ZrO_2$ | $SO_4^{2-}$ | 87.53:12.47 | 90.0:10.0 | 87.53:12.47 | −16.04 | C |
| 9 | $ZrO_2$ | $PO_4^{3-}$ | 89.37:10.63 | 91.6:8.4 | 89.37:10.63 | −11.99 | C |
| 10 | — | $WO_3$ | 0:100 | — | 0:100 | — | A |

TABLE 2

| Sample No. | Specific surface area ($m^2/g$) | Element temperature (control temperature) (° C.) | Measurement results of ammonia sensitivity | Acid content (mmol/g) |
|---|---|---|---|---|
| 1 | 22.5 | 350 | FIG. 6 | — |
| 2 | 35.3 | 350 | FIG. 7 | 0.071 |
| 3 | 47.4 | 350, 400 | FIG. 8, FIG. 9 | 0.107 |
| 4 | 43.1 | 350 | FIG. 10 | — |
| 5 | 76.3 | 350, 450 | FIG. 11, FIG. 12 | 0.224 |
| 6 | 94.8 | 350 | FIG. 13 | — |
| 7 | 312 | 350 | FIG. 14 | — |
| 8 | 54.3 | 350 | FIG. 15 | 0.178 |
| 9 | 96.1 | 350 | FIG. 16 | — |
| 10 | 0.6 | 350 | FIG. 18 | — |

Test Example 1

In the present Test Example, ammonia sensors (sample Nos. 1 through 10) were produced, each including a sensitive layer formed from a material produced by any of the above-described production methods (synthesis methods A, B, and C).

The specific surface area of the raw material powder for the sensitive layer of each of the samples was measured by means of the BET method; i.e., the specific surface area of the $ZrO_2$ powder (primary component) for the sensitive layer of each of sample Nos. 1 through 9, and the specific surface area of the $WO_3$ powder (secondary component) for the sensitive layer of sample No. 10 were measured. Specifically, the specific surface area was measured by means of the $N_2$ gas adsorption BET method using a Multisorb 12 (product of Yuasa Ionics Inc.), in which each of the above powders was exposed to the flow of a gas mixture of He and $N_2$ at 200° C. for 60 minutes. The results are shown in Table 2.

Each of the ammonia sensors was mounted in the evaluation apparatus, a gas containing $NH_3$ (concentration of $NH_3$: 0, 5, 20, 50, 100, or 150 ppm) was supplied to the evaluation apparatus, and the impedance (Z) of the ammonia sensor was obtained under the following conditions: gas temperature: 280° C., element temperature: 350° C., 400° C., or 450° C. The results are shown in FIGS. 6 through 16. Each of the figures shows Sample No. and the element operation temperature.

As is clear from FIGS. 6 through 16, the ammonia sensors of the present invention (samples Nos. 1 through 5 and 7 through 9), each including the sensitive layer formed from the solid, super-strong acidic substance, exhibited good concentration-dependent sensitivity to ammonia of different concentrations.

In contrast, as shown in FIG. 13, the comparative ammonia sensor (sample No. 6), in which the sensitive layer contained only the primary component, exhibited no change in sensitivity to ammonia of different concentrations. The results of evaluation of the comparative ammonia sensor (sample No. 10), in which the sensitive layer contained only the secondary component, will be described in Test Example 2.

As is clear from the test results shown in FIG. 6 (sample No. 1) through FIG. 12 (sample No. 5), when the incorporation amount of $WO_3$ (secondary component) is increased, the base impedance as measured when $NH_3$ is 0 ppm decreases, and the $NH_3$ sensitivity (the rate of change in impedance) increases since the acid content increases as described below. Small base impedance is advantageous in designing a sensor control circuit.

As is clear from the test results shown in FIGS. 11 and 12 (sample No. 5), when the incorporation amount of $WO_3$ (secondary component) is large; i.e., when the acid content is high, even if the element operation temperature (element control temperature) is increased, the ammonia sensor exhibits sufficient sensitivity. Therefore, even when employed in a high-temperature atmosphere (e.g., exhaust gas), the ammonia sensor advantageously exhibits sufficient sensitivity.

Test Example 2

In the present Test Example, the effect of interference gases on the ammonia sensor was investigated.

In the present Test Example, the ammonia sensor of the present invention (sample No. 3) was employed.

In the present Test Example, $NO_2$, NO, CO, $C_3H_6$, and $NH_3$ (100 ppm each, $C_3H_6$: 100 ppmC) were brought into the evaluation apparatus, and the sensitivity of the ammonia sensor to ammonia was evaluated under the following conditions: gas temperature: 280° C., element temperature: 350° C. The results are shown in FIG. 17.

FIGS. 17 and 18 are comparative graphs showing the sensitivity to each of the above gases when the sensitivity to $NH_3$ (100 ppm) is taken as 100.

As is clear from FIG. 17, the ammonia sensor of the present invention exhibited high sensitivity to $NH_3$ and very low sensitivity to other interference gases; i.e., the ammonia sensor exhibits excellent ammonia selectivity.

The test results of the comparative ammonia sensor (sample No. 10), in which the sensitive layer contained only $WO_3$ (secondary component), are shown in FIG. 18.

As shown in FIG. 18, the ammonia sensor (sample No. 10), in which the sensitive layer contained only $WO_3$ (secondary component), exhibited sensitivity to different gases, and therefore does not selectively detect $NH_3$.

Test Example 3

In the present Test Example, the effect of a Pt resistor on control of the element temperature was investigated.

In the present Test Example, the ammonia sensor of the present invention (sample No. 3) was employed.

In the present Test Example, in order to keep the element temperature constant, the element temperature is regulated by use of a Pt resistor (i.e., a temperature sensor, which is a temperature measuring resistor).

Specifically, while the element temperature was regulated to 400° C., a gas (temperature: 300° C. or 400° C., $NH_3$ concentration: 0, 5, 20, 50, 100, or 200 ppm) was supplied to the evaluation apparatus, and the impedance (Z) of the ammonia sensor was measured. The above procedure was repeated, except that the element temperature was not regulated. The results are shown in FIGS. 19 and 20. FIG. 19 is a graph showing the gas temperature dependency of the $NH_3$ sensitivity in the case where element temperature is not regulated; and FIG. 20 is a graph showing the gas temperature dependency of the $NH_3$ sensitivity in the case where element temperature is regulated.

As is clear from FIGS. 19 and 20, when the element temperature is regulated by use of a Pt resistor, the element temperature is maintained constant even in gases of different temperatures, and thus the temperature dependency of the $NH_3$ sensitivity is reduced. In contrast, when the element temperature is not regulated, the temperature dependency of the $NH_3$ sensitivity increases.

Test Example 4

In the present Test Example, the relation between acid content, element temperature, and $NH_3$ sensitivity was investigated.

Now, $NH_3$-TPD measurement performed on the sensitive layer of the ammonia sensor (sample No. 3) will be described.

FIG. 21 shows data obtained by the TPD measurement. The peak end temperature (i.e., T) was estimated to be 450° C. from the mountain-shaped ammonia-temperature programmed desorption curve. The peak end temperature T represents acid strength ($NH_3$ adsorption strength).

By utilizing a temperature programmed desorption curve as shown in FIG. 21, the acid characteristics of a substance (sample) can be evaluated. Specifically, the acid content and the acid strength of the substance can be readily estimated from the integral area and the peak end temperature, respectively. However, these values vary in accordance with test conditions (e.g., the amount of the sample), and thus are not necessarily specific to the substance.

For example, as shown in Table 1, the acid contents of sample Nos. 2, 3, and 5 can be estimated to be 0.071 mmol/g, 0.107 mmol/g, and 0.224 mmol/g, respectively.

In the present Test Example, the impedance (Z) of the ammonia sensor (sample No. 5) was measured in a gas containing $NH_3$ whose concentration was varied in a stepwise manner from 0 to 5, 20, 100, 150, and 0 ppm at a predetermined interval (200 seconds) under the following conditions: gas temperature: 280° C., element temperature: 350° C. or 450° C. The results are shown in FIGS. 22 and 23. FIGS. 22 and 23 are graphs showing the responsiveness of the sensor to $NH_3$ gas at the respective element temperatures.

As is clear from FIGS. 22 and 23, when the element temperature is increased, the $NH_3$ adsorption/desorption rate becomes high, and thus the sensor exhibits enhanced responsiveness.

Also, as is clear from FIGS. 8 and 9 showing the relationship between the sensitivity and the element temperature of the ammonia sensor (sample No. 3), in which the incorporation amount of the secondary component is small and the acid content is low; FIGS. 11 and 12 showing the relationship between the sensitivity and the element temperature of the ammonia sensor (sample No. 5), in which the incorporation amount of the secondary component is high and the acid content is high; and FIGS. 22 and 23 showing the relationship between the responsiveness and the element temperature of the ammonia sensor (sample No. 5), the ammonia sensor in which the acid content is high detects the $NH_3$ concentration at high accuracy even at a high regulation temperature.

When the incorporation amount of the secondary component is increased, the acid content increases, and as a result, the $NH_3$ sensitivity is enhanced. When the $NH_3$ sensitivity is high, the operation temperature of the ammonia sensor (the element temperature) can be increased. That is, although the $NH_3$ sensitivity decreases in accordance with an increase in the sensor operation temperature, when the acid content is large, the sensor exhibits sufficient $NH_3$ sensitivity, and thus the sensor operation temperature can be increased. Therefore, the responsiveness of the sensor can be enhanced.

As described above, the optimum operation temperature of the ammonia sensor can be increased by increasing the incorporation amount of the secondary component; i.e., by increasing the acid content. Therefore, the temperature required for operation of the sensor is determined in accordance with the environment in which the sensor is employed (preferably, the sensor is operated at a temperature higher than that of the environment in order to avoid the effect of the environmental temperature on the sensor), and the composition of the primary and secondary components is determined such that the sensor can be operated at the above-determined temperature, to thereby optimize the design of the sensor.

As described above, when the acid content increases, the base impedance of the ammonia sensor as measured when $NH_3$ is 0 ppm decreases. Small base impedance is advantageous in designing a sensor control circuit.

In the above-described Test Examples, $TiO_2$ or $ZrO_2$ was employed as the primary component of the super-strong acidic metal oxide, and $WO_3$, $SO_4^{2-}$, or $PO_4^{3-}$ was employed as the secondary component of the metal oxide. However, the primary component may be selected from among $Fe_2O_3$, $HfO_2$, $SnO_2$, $Al_2O_3$, and $SiO_2$, and the secondary component may be selected from among $MoO_3$ and $B_2O_3$. This is because these oxides are considered to exhibit characteristics similar to those of the components of the super-strong acidic metal oxide employed in the Test Examples.

Second Embodiment

The ammonia sensor of the second embodiment will next be described. Repeated description of components which are common between the ammonia sensors of the first and second embodiments is omitted.

The ammonia sensor of the second embodiment differs from that of the first embodiment in the configuration of the sensor element member.

a) The configuration of the ammonia sensor of the present embodiment will now be described. FIG. 24 is a perspective view of an essential portion of the ammonia sensor (sensor element member) and an exploded perspective view of the essential portion. FIG. 25 is a cross-sectional view of the essential portion shown in FIG. 1, as taken along line B-B'.

As shown in FIG. 24, an element section 103 of a sensor element member 102 constituting the essential portion of the ammonia sensor 101 of the present embodiment includes an insulating substrate 105 on which the below-described components are successively laminated.

Specifically, a pair of lead portions 107 and 109 which predominantly contain platinum are provided on the insulating substrate 105 formed of alumina; a lower electrode 111 is provided on the substrate 105 so as to be connected to the lead portion 107; a sensitive layer 113 is provided on the lower electrode 111 so as to cover the entirety of the electrode 111; an upper electrode 115 is provided on the sensitive layer 113 so as to be connected to the lead portion 109; and a protective layer 117 is provided on the upper electrode 115 so as to cover the entirety of the electrode 115 and the entirety of a portion of the sensitive layer 113 that is exposed at the periphery of the electrode 115.

As in the case of the first embodiment, the sensitive layer 113 (thickness: about 30 µm) formed by thick-film printing contains a porous gas-sensitive material (i.e., a solid, super-strong acidic substance).

Preferably, the lower electrode 111 and the upper electrode 115 are formed from a porous electrode material having a porosity larger than that of the material of the sensitive layer 113, such that the electrodes 111 and 115 do not impede diffusion of a sample gas to the sensitive layer 113.

As shown in FIG. 25, a heater 119 for heating the element section 103 and a temperature sensor 120, which is a temperature-measuring resistor, are provided in the interior of the insulating substrate 105.

The ammonia sensor 101 of the present embodiment exhibits effects similar to those obtained from the ammonia sensor of the first embodiment. In the ammonia sensor 101, the upper electrode 115 may serve as a protective layer for the sensitive layer 113.

Third Embodiment

The ammonia sensor of the third embodiment will next be described. Repeated description of components which are common among the ammonia sensors of the first, second, and third embodiments is omitted.

The ammonia sensor of the present embodiment differs from that of the first or second embodiment in the configuration of a sensitive layer.

a) The configuration of the sensor element member of the ammonia sensor of the present embodiment will now be described.

In the present embodiment, a sensitive layer (not illustrated) is formed of a composite oxide containing a $ZrO_2$ carrier (primary component) and $WO_3$ (secondary component) which is bonded to the surface of the carrier. The $ZrO_2$ carrier contains a predetermined amount of $Y_2O_3$ serving as an agent for stabilizing the crystal structure of $ZrO_2$, and $ZrO_2$ and $Y_2O_3$ together form a solid solution.

In the present embodiment, $WO_3$ is employed as the secondary component, but the secondary component may be at least one species selected from among $WO_3$, $MoO_3$, $B_2O_3$, $SO_4^{2-}$ and $PO_4^{3-}$. The stabilizing agent is not necessarily limited to $Y_2O_3$, and may be at least one species selected from among CaO, MgO, $Y_2O_3$, $Yb_2O_3$ and $Ga_2O_3$.

Since the composite oxide employed in the present embodiment has a structure in which $ZrO_2$ and $Y_2O_3$ form a solid solution in the crystal phase of $ZrO_2$ serving as the primary component, the stability of the crystal phase is high, and the composite oxide exhibits excellent thermal resistance and durability. Therefore, even when the ammonia sensor is employed at a high temperature (e.g., 400° C. or higher) over a long period of time, the sensitivity of the sensor is not lowered, and the sensor provides consistent output.

That is, in the present embodiment, $Y_2O_3$ is incorporated into the crystal phase of $ZrO_2$ such that $ZrO_2$ and $Y_2O_3$ form a solid solution, thereby stabilizing the crystal phase of $ZrO_2$. This structure enables suppression of change in the crystal structure, whereby the secondary component is reliably bonded to the surface of the carrier. Therefore, even when the ammonia sensor is employed at a high temperature over a long period of time, the sensitivity of the sensor is not lowered, and the sensor provides consistent output.

b) Next, the method for producing the ammonia sensor of the present embodiment (particularly, the method for synthesizing the material of the sensitive layer constituting the sensor element member) will be described. The production method will be described by taking, as an example, production of an ammonia sensor employed in the below-described Test Examples.

(Synthesis of Powder)

Zirconium oxynitrate and yttrium nitrate were dissolved in $H_2O$, and aqueous ammonia was added to the resultant solution, to thereby adjust the pH of the solution to 8. The amount of yttrium nitrate was regulated such that the Y content of the target product (i.e., $ZrO_2$—$Y_2O_3$ powder) was 1) 2.7 mol %, 2) 4 mol %, or 3) 8 mol % as reduced to $Y_2O_3$. The thus-obtained precipitate was subjected to suction-filtration and washing, and then dried in a drying machine at 110° C. for 24 hours. Subsequently, the thus-dried product was fired in a muffle furnace at 400° C. for 24 hours, to thereby yield a $ZrO_2$—$Y_2O_3$ powder (which was to serve as a carrier) having a large specific surface area.

Separately, ammonium tungstate was weighed such that the W content of the target product (i.e., $WO_3/ZrO_2$—$Y_2O_3$ powder) was 10 wt. % as reduced to $WO_3$, and the thus-weighed ammonium tungstate was dissolved in $H_2O$. Aqueous ammonia was added to the resultant solution, to thereby adjust the pH of the solution to 10 to 11. A predetermined amount of the above-obtained $ZrO_2$—$Y_2O_3$ powder was added to the resultant solution, and sufficiently stirred, to thereby prepare a suspension. The suspension was subjected to evaporation to dryness by use of a rotary evaporator. The thus-obtained solid was dried in a drying machine at 120° C. for 24 hours, followed by firing in a muffle furnace at 800° C. for five hours.

Through the above-described procedure, the target product (i.e., $WO_3/ZrO_2$—$Y_2O_3$ powder having a $WO_3$ content of 10 wt. %) was obtained. The powder was employed in the below-described Test Examples. The specific surface area of the thus-obtained powder was measured by means of the BET method. The results are shown in Table 3.

In addition, the above synthesis procedure was repeated, except that addition of yttrium nitrate was not performed during the course of preparation of a carrier, to thereby yield a $WO_3/ZrO_2$ powder having a $WO_3$ content of 10 wt. % and containing no $Y_2O_3$ (i.e., a comparative product employed in the below-described Test Examples). The specific surface area of the thus-obtained powder was also measured by means of the BET method. The results are shown in Table 3. Sample (4) shown in Table 3 falls within the scope of the present invention.

TABLE 3

| Sample | Material of sensitive layer | Specific surface area (m²/g) |
|---|---|---|
| (1) | $WO_3/ZrO_2$.2.7 mol % $Y_2O_3$ | 48.6 |
| (2) | $WO_3/ZrO_2$.4 mol % $Y_2O_3$ | 49.0 |
| (3) | $WO_3/ZrO_2$.8 mol % $Y_2O_3$ | 35.7 |
| (4) | $WO_3/ZrO_2$ | 47.4 |

In each of the above samples, the $WO_3$ content was 10 wt. % based on the total amount (100 wt. %) of $ZrO_2$—$Y_2O_3$ (or $ZrO_2$) and $WO_3$.

(Production of Sensor Element Member)

Subsequently, each of the powders synthesized as described above, an organic solvent, and a dispersant were placed in a mortar, and disperse-mixed by use of a smash-mixing machine for four hours. Thereafter, a binder was added to the resultant mixture, and wet-mixed for four hours, to thereby prepare a slurry. The viscosity of the resultant slurry was regulated, to thereby yield a paste.

In a manner similar to that of the first embodiment, the thus-obtained paste was applied by screen printing onto an insulating substrate having, on its surface, a pair of comb-shaped electrodes, so as to form a thick film. The material of the comb-shaped electrodes may be, for example, Au, a noble metal other than Au, a noble metal alloy, or a mixture of noble metals.

Thereafter, the paste was dried at 60° C., and then baked on the insulating substrate at 600° C. for one hour, to thereby produce a sensor element member of an ammonia sensor.

c) Next, Test Examples, in which the effects of the ammonia sensor of the present embodiment were confirmed, will be described.

Test Example 5

In the present Test Example, the durability of the ammonia sensor was evaluated.

(i) Evaluation Apparatus (Gas Measuring Apparatus)

A sample gas generation apparatus similar to that employed in Test Example 1 was employed for evaluation of the ammonia sensor. The ammonia sensor was subjected to evaluation under the following measurement conditions.

<Measurement Conditions>
Gas temperature: 280° C.
Element temperature: 350° C.
Gas composition: $O_2$: 10 vol. %, $CO_2$: 5 vol. %,
$H_2O$: 5 vol. %, $NH_3$: 0 to 200 ppm,
$N_2$: balance The ammonia sensor to be tested was placed in the evaluation apparatus and exposed to the gas flowing through the apparatus, a predetermined alternating voltage (2 V) at a predetermined frequency (400 Hz) was applied to the electrode leads of the ammonia sensor, and the impedance of the ammonia sensor (i.e., the sensitive layer) was obtained from a current flowing between the electrode leads.

In a manner similar to that of Test Example 1, $NH_3$ sensitivity was obtained by measuring the impedance of the sensor as measured in a gas containing 0 ppm $NH_3$ and the impedance of the sensor as measured in a gas containing $NH_3$ of different concentrations.

(ii) Evaluation of Sensor Durability

For evaluation of sensor durability, an ammonia sensor incorporating a sensor element member including a sensitive layer formed of each of samples (1) through (4) shown in Table 3 has prepared. The thus-prepared ammonia sensor (hereinafter called an "untreated ammonia sensor") was employed as a test sample.

Separately, an ammonia sensor was prepared by the following procedure: a sensor element member including a sensitive layer formed of each of samples (1) through (4) shown in Table 3 was thermally treated (specifically, the sensor element member was heated in a small-sized heating furnace at 600° C. for 100 hours); and the thus-treated sensor element member was assembled into an ammonia sensor. The thus-prepared ammonia sensor (hereinafter called an "endured ammonia sensor") was employed as a test sample.

Subsequently, the above-prepared untreated and endured ammonia sensors were mounted in the aforementioned evaluation apparatus, to thereby evaluate the performance of the respective sensors. Specifically, the concentration of ammonia in the gas was varied, and the sensitivity, as measured based on variation in impedance, was obtained for each of the ammonia sensors. The results are shown in FIG. 26.

As is clear from FIG. 26, regarding the ammonia sensors including the sensitive layers formed of samples (1) through (3); i.e., the ammonia sensors including the sensitive layers formed of $ZrO_2$ stabilized by $Y_2O_3$, variation in ammonia sensitivity between untreated and endured sensors is small, and even the endured ammonia sensor maintains sensitivity at a high level (comparable with the untreated ammonia sensor) and exhibits excellent thermal resistance and durability.

When the $Y_2O_3$ content of the sensitive layer is high, lowering of the sensitivity of the ammonia sensor tends to be suppressed. Particularly, in the ammonia sensor including the sensitive layer formed of sample (3) in which $Y_2O_3$ was incorporated in an amount of 8 mol % such that $ZrO_2$ and $Y_2O_3$ form a solid solution, no lowering of the sensitivity was observed.

In contrast, regarding the ammonia sensors including the sensitive layers formed of sample (4) (sample for comparison); i.e., the ammonia sensors including the sensitive layers formed of $ZrO_2$ which was not stabilized by $Y_2O_3$, the endured ammonia sensor exhibited considerably lowered sensitivity as compared with the untreated ammonia sensor.

Test Example 6

In the present Test Example, changes in crystal structure were investigated.

In the present Test Example, a paste was prepared from each of samples (1) through (4) shown in Table 3, and the paste was applied by printing onto an alumina plate (size: 5 cm×5 cm) and fired at 600° C. for one hour, to thereby prepare a thick film sample (hereinafter also called an "untreated sample").

Separately, thick film samples were formed in a manner similar to that described above, and each of the samples was heated in a small-sized heating furnace at 600° C. for 100 hours, to thereby prepare a thermally treated thick film sample (hereafter also called an "endured sample").

Subsequently, only the detection material (formed of each of samples (1) through (4)) was collected from each of the above-prepared untreated and endured samples formed on the alumina plates, and the thus-collected powdery material was subjected to XRD measurement by use of a RU-200 (product of RIGAKU). The results are shown in FIG. 27.

In the XRD patterns shown in FIG. 27, peaks at 28° and 31.5° correspond to monoclinic $ZrO_2$, and a peak at 30° corresponds to tetragonal $ZrO_2$ or cubic $ZrO_2$.

As is clear from FIG. 27, regarding the thick film samples formed of samples (1) through (3); i.e., the samples formed of $ZrO_2$ stabilized by $Y_2O_3$, in the case of the endured sample, as compared with the case of the untreated sample, a change in the crystal phase (from monoclinic crystals to tetragonal or cubic crystals) is suppressed, and the endured sample maintains a stable crystal structure.

When the $Y_2O_3$ content is high, the stability of the crystal structure tends to increase. Particularly, the thick film samples formed of sample (3) containing completely stabilized $ZrO_2$, in which $Y_2O_3$ is incorporated in an amount of 8 mol % such that $ZrO_2$ and $Y_2O_3$ form a solid solution, have a crystal structure of very high stability (substantially no peak corresponding to monoclinic $ZrO_2$ is observed for the endured sample).

In contrast, regarding the thick film samples formed of sample (4) (sample for comparison); i.e., the samples formed of $ZrO_2$ which was not stabilized by $Y_2O_3$, in the case of the endured sample, the amount of tetragonal crystals is considerably reduced, and crystal phase transition from tetragonal crystals to more stable monoclinic crystals occurs at ambient temperature.

As is clear from the results of Test Examples 5 and 6, when an ammonia sensor incorporates a selective layer formed of a material prepared by adding a stabilizing agent (e.g., $Y_2O_3$) to $ZrO_2$, the ammonia sensor exhibits excellent long-term stability even at a high temperature.

Fourth Embodiment

The ammonia sensor of the fourth embodiment will next be described. Repeated description of components which are common among the ammonia sensors of the first, second, third, and fourth embodiments is omitted.

The ammonia sensor of the present embodiment differs from that of the first, second, or third embodiments with respect to a casing of the ammonia sensor into which a sensor element member is to be incorporated and the internal configuration of the sensor.

The entire configuration of the ammonia sensor of the present embodiment, which is an assembly incorporating a sensor element member, will now be described.

As shown in FIG. 28, in the ammonia sensor 121 of the present embodiment, a sensor element member 123 which, at its front-end portion (the lower portion as viewed in FIG. 28), includes an element section (not illustrated). The rear-end portion (the upper portion as viewed in FIG. 28) of the sensor element member 123 is connected to a first end portion of each of metallic plates 125. A second end portion of each of the metallic plates 125 is connected via a connection terminal 127 to a lead wire 129.

A ceramic holder 131, a talc powder 133, and an insulating protector 135 are provided around the sensor element member 123 from the front-end portion toward the rear-end portion of the member 123, and the ceramic holder 131, the talc powder 133, and the insulating protector 135 are accommodated in a main fitting 137.

The front-end portion of the sensor element member 123 is protected by a porous protector 139 supported by the main fitting 137. The first end portion of the metallic plate 125, which has a wavy form, is sandwiched between the rear-end portion of the sensor element member 123 and the insulating protector 135, whereby the metallic plate 125 is in contact with the sensor element member 123.

Furthermore, an outer tube 141 is fitted around the main fitting 137 so as to cover the periphery of the rear-end portion of the ammonia sensor 121, and a ceramic separator 143 in which the lead wire 129 is inserted and a grommet 145 are fitted in the rear-end portion of the outer tube 141. The connection terminal 127 is provided in the ceramic separator 143, and the rear-end of the outer tube 141 is sealed with the grommet 145.

The ammonia sensor 121 of the present embodiment, having the above-described configuration, exhibits effects similar to those obtained from the ammonia sensor of the first embodiment.

Needless to say, the present invention is not limited to the above-described embodiments, and various modifications may be performed without departing from the scope of the present invention.

For example, the heater is not necessarily combined with the element section, and may be provided separately from the element section. The platinum resistor and the heater may be vertically inverted.

This application is based on Japanese Patent Appln. No. 2002-279680 filed Sep. 25, 2002, Japanese Patent Appln. No. 2003-51346 filed Feb. 27, 2003, and Japanese Patent Appln. No. 2003-275327 filed Jul. 16, 2003, each of which is incorporated herein by reference in its entirety.

What is claimed is:

1. An ammonia sensor for detecting ammonia in a gas, comprising a pair of electrodes and a sensitive section contacting the paired electrodes, the sensitive section comprising a solid, super-strong acidic substance;
    wherein the solid, super-strong acidic substance has an acidity of $\leq -11.93$ as determined by Hammett acidity function $H_0$, and
    wherein the solid, super-strong acidic substance comprises a primary component containing a $ZrO_2$ carrier and a secondary component containing an oxide or an oxide ion, the primary and secondary components being chemically bonded to one another.

2. The ammonia sensor as claimed in claim 1, wherein the secondary component contains at least one species selected from the group consisting of $WO_3$, $MoO_3$, $B_2O_3$, $SO_4^{2-}$ and $PO_4^{3-}$.

3. The ammonia sensor as claimed in claim 2, wherein the carrier contains an agent for stabilizing the crystal structure of $ZrO_2$ and the crystal-structure-stabilizing agent comprises at least one species selected from the group consisting of CaO, MgO, $Y_2O_3$, $Yb_2O_3$ and $Ga_2O_3$.

4. The ammonia sensor as claimed in claim 2, wherein the $ZrO_2$ carrier contains at least 4 mol % $Y_2O_3$.

5. The ammonia sensor as claimed in claim 2, wherein the $ZrO_2$ carrier contains at least 6 mol % $Y_2O_3$.

6. The ammonia sensor as claimed in claim 1, wherein the solid, super-strong acidic substance has an acid content of at least 0.05 mmol/g.

7. The ammonia sensor as claimed in claim 1, wherein when the total amount of the primary and secondary components is taken as 100 mol %, the amount of the secondary component is 1 to 25 mol %.

8. The ammonia sensor as claimed in claim 1, wherein the secondary component comprises W in an amount of 1.5 to 30 wt. % as reduced to $WO_3$.

9. The ammonia sensor as claimed in claim 1, further comprising a protective layer covering the sensitive section.

10. The ammonia sensor as claimed in claim 1, further comprising a heater for heating the element section.

11. The ammonia sensor as claimed in claim 10, further comprising an element temperature detection means for detecting the temperature of the element section, and a temperature regulation means for controlling the heater such that the element temperature falls within a predetermined temperature range.

12. The ammonia sensor as claimed in claim 1, further comprising an insulating substrate and a heater embedded in the insulating substrate, wherein the paired electrodes are formed on the insulating substrate and the sensitive section is formed on the paired electrodes so as to cover the paired electrodes.

13. The ammonia sensor as claimed in claim 12, further comprising an element temperature detection means for detecting the temperature of the element section, and a temperature regulation means for controlling the heater such that the element section temperature falls within a predetermined temperature range.

14. The ammonia sensor as claimed in claim 1, further comprising an insulating substrate and a heater embedded in the substrate, wherein said paired electrodes comprise a lower electrode and an upper electrode, the lower electrode is formed on the insulating substrate, the sensitive section is formed on the lower electrode so as to cover the lower electrode, and the upper electrode is formed on the sensitive section.

15. The ammonia sensor as claimed in claim 14, further comprising an element temperature detection means for detecting the temperature of the element section, and a temperature regulation means for controlling the heater such that the element section temperature falls within a predetermined temperature range.

16. The ammonia sensor as claimed in claim 1, wherein the sensitive section consists essentially of the solid, super-strong acidic substance.

17. The ammonia sensor as claimed in claim 1, wherein the sensitive section consists of the solid, super-strong acidic substance.

18. An ammonia sensor for detecting ammonia in a gas, comprising a pair electrodes and a sensitive section contacting the paired electrodes, the sensitive section comprising a solid, super-strong acidic substance;

wherein the solid, super-strong acidic substance has an acidity of $\leq -11.93$ as determined by Hammett acidity function $H_0$, and wherein the solid, super-strong acidic substance comprises a primary component containing $TiO_2$ and a secondary component containing $SO_4^{2-}$, the primary and secondary components being chemically bonded to one another.

19. The ammonia sensor as claimed in claim 18, further comprising a protective layer covering the sensitive section.

20. The ammonia sensor as claimed in claim 18, further comprising a heater for heating the element section.

21. The ammonia sensor as claimed in claim 20, further comprising an element temperature detection means for detecting the temperature of the element section, and a temperature regulation means for controlling the heater such that the element temperature falls within a predetermined temperature range.

22. The ammonia sensor as claimed in claim 18, further comprising an insulating substrate and a heater embedded in the insulating substrate, wherein the paired electrodes are formed on the insulating substrate and the sensitive section is formed on the paired electrodes so as to cover the paired electrodes.

23. The ammonia sensor as claimed in claim 22, further comprising an element temperature detection means for detecting the temperature of the element section, and a temperature regulation means for controlling the heater such that the element section temperature falls within a predetermined temperature range.

24. The ammonia sensor as claimed in claim 18, further comprising an insulating substrate and a heater embedded in the substrate, wherein said paired electrodes comprise a lower electrode and an upper electrode, the lower electrode is formed on the insulating substrate, the sensitive section is formed on the lower electrode so as to cover the lower electrode, and the upper electrode is formed on the sensitive section.

25. The ammonia sensor as claimed in claim 24, further comprising an element temperature detection means for detecting the temperature of the element section, and a temperature regulation means for controlling the heater such that the element section temperature falls within a predetermined temperature range.

26. The ammonia sensor as claimed in claim 18, wherein the sensitive section consists essentially of the solid, super-strong acidic substance.

27. The ammonia sensor as claimed in claim 18, wherein the sensitive section consists of the solid, super-strong acidic substance.

* * * * *